United States Patent
Iwata et al.

(10) Patent No.: US 6,740,662 B1
(45) Date of Patent: May 25, 2004

(54) NAPHTHYRIDINE DERIVATIVES

(75) Inventors: Masahiro Iwata, Tsukuba (JP); Noriyuki Kawano, Tsukuba (JP); Tomofumi Takuwa, Tsukuba (JP); Ryota Shiraki, Tsukuba (JP); Miki Kobayashi, Tsukuba (JP); Makoto Takeuchi, Tsukui (JP)

(73) Assignee: Yamanouchi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/111,077

(22) PCT Filed: Oct. 24, 2000

(86) PCT No.: PCT/JP00/07433
§ 371 (c)(1),
(2), (4) Date: Apr. 19, 2002

(87) PCT Pub. No.: WO01/30779
PCT Pub. Date: May 3, 2001

(30) Foreign Application Priority Data

Oct. 25, 1999 (JP) ............................................. 11/302544

(51) Int. Cl.$^7$ ..................... A61K 31/435; C07D 471/04
(52) U.S. Cl. ........................ 514/300; 546/122; 546/123
(58) Field of Search ................. 546/122, 123; 514/300

(56) References Cited

U.S. PATENT DOCUMENTS 4,324,893 A    4/1982   Scotese et al.

FOREIGN PATENT DOCUMENTS

| | | |
|---|---|---|
| EP | 0 670 320 A1 | 9/1995 |
| EP | 0 779 292 A1 | 6/1997 |
| EP | 0 842 933 A1 | 5/1998 |
| EP | 0 947 515 A1 | 10/1999 |
| EP | 1 086 948 A1 | 3/2001 |
| JP | 55-164682 A | 12/1980 |
| JP | 7-10875 | 1/1995 |
| JP | 7-126268 | 5/1995 |

OTHER PUBLICATIONS

European Search Report dated Apr. 17, 2003.
International Search Report.
Matsuura Akihiro et al., "Substituted 1, 8–naphthyridin–2(1H)–ones as selective phosphodiesterase IV inhibitors". Biol. Pharm. Bull. 1994, vol. 17, No. 4, pp. 498–503, abstract; Table I–III.
Lorne Davies et al., 2,3–Disubstituted 1,8–naphthyridines as Potential Diuretic Agents. 3.4– and 7–Phenyl Derivatives, Eur. J. Med. Chem. –Chim. Ther., (1985), vol. 20, No. 4, pp. 381–383.
Arhtur A. Santilli et al., 2–Oxo–1, 8–Napthyridine–3–Carboxylic Acid Derivates with Potent Gastric Antisecretory Properties, J. Med. (1987), vol. 30, No. 12, pp. 2270–2277.

*Primary Examiner*—Bernard Dentz
(74) *Attorney, Agent, or Firm*—Sughrue Mion, PLLC

(57) ABSTRACT

2-Oxo-1,2-dihydro-1,8-naphthyridine derivatives characterized by bearing a specific substituent, —X—$R^6$, at the 3-position and a cyclic substituent, $R^5$, at the 4-position; or salts thereof. The derivatives and the salts are useful as drugs, particularly preventive or therapeutic agents for respiratory diseases related to PDE IV.

8 Claims, No Drawings

NAPHTHYRIDINE DERIVATIVES

This application is a 371 of PCT/JP00/07433 filed Oct. 24, 2000.

TECHNICAL FIELD

The present invention relates to a naphthyridine derivative useful as a medicament, particularly as a type IV phosphodiesterase inhibitor.

BACKGROUND ART

Asthma is a respiratory disease which repeats wheeze and attack by the contraction of airway. The number of the patients has been increasing steadily and is predicted to further increase hereafter.

Xanthine derivatives such as aminophylline and theophylline and β-stimulators such as procaterol are now mainly used as bronchodilator for the treatment of asthma.

The functional mechanism of these compounds is to alleviate contraction of airway smooth muscle by increasing intracellular cyclic adenosine 3',5'-monophosphate (cAMP) concentration through the activation of an intracellular cAMP producing enzyme, adenylate cyclase, or the inhibition of a cAMP hydrolyzing enzyme, phosphodiesterase (PDE) in airway smooth muscle (*Internal Medicine*, 69, 207–214 (1992)).

It is known that increased intracellular cAMP concentration induces inhibition of the contraction of airway smooth muscle (*Clin. Exp. Allergy*, 22, 337–344 (1992), *Drugs of the Future*, 17, 799–807 (1992)), which is useful in improving conditions of asthma.

However, it is known that the xanthine derivatives express systemic side effects such as hypotension and cardiotonic action (*J. Cyclic Nucleotide and Protein Phosphoxylation Res.*, 10, 551–564 (1985), *J. Pharmacol. Exp. Ther.*, 257, 741–747 (1991)), and the β-stimulators are apt to cause desensitization and, when the dosage is increased, generate side effects such as finger tremor and palpitation.

On the other hand, it has been revealed that PDE is divided into at least five different types of from I to V, and each of them has different distribution or function (*Pharmacol. Ther.*, 51, 13–33 (1991)). Particularly, type IV PDE does not act upon cyclic guanosine 3',5'-monophosphate (cGMP) but specifically hydrolyze cAMP among nucleotides, and its presence is recognized in both of airway smooth muscle and infiltrating cells.

Also, it has been reported that type IV PDE inhibitors show inhibitory action upon eosinophiles infiltration by antigens and platelet-activating factors in guinea pig (*Eur. J. Pharmacol.*, 255, 253–256 (1994)) and inhibit liberation of detrimental proteins (MBP, ECP) from eosinophiles (*Br. J. Pharmacol.*, 115, 39–47 (1995)). It has been also reported that they show inhibitory action upon the contraction of airway smooth muscle by contractile substances (histamine, methacholine, $LTD_4$) (*Br. J. Pharmacol.*, 113, 1423–1431 (1994)), inhibit production of IL-4, a cytokine which is said to deeply participate in asthma (*J. Invest. Dermatol.*, 100, 681–684 (1993)), express inhibitory action upon the acceleration of vascular permeability in the airway (*Fundam. Clin. Pharmacol.*, 6, 247–249 (1992)) and show inhibitory action upon airway hypersensitivity (*Eur. J. Pharmacol.*, 275, 75–82 (1995)). Thus, it is expected that a type IV PDE inhibitor will become an asthma-treating agent having less side effects.

As compounds having type IV PDE inhibitory activity, a large number of compounds are known including naphthyridine derivatives. The present applicant has previously reported a naphthyridine derivative represented by the following formula in which the 4-position ($R^6$) is a cyclic substituent such as an aryl, a heteroaryl or a cycloalkyl and the 3-position ($R^5$) is unsubstituted or a substituted lower alkyl group (WO 96/06843).

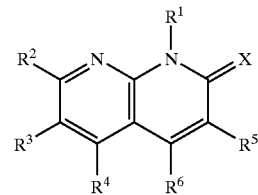

(wherein $R^5$ represents a hydrogen atom or a lower alkyl group and $R^6$ represents an aryl group having a substituent, a heteroaryl group having a substituent, a cycloalkyl group or an adamantyl group. See the reference for other details.)

DISCLOSURE OF THE INVENTION

The present inventors have conducted studies with the aim of providing a novel compound which efficiently and selectively inhibits type IV PDE and is useful for preventing and treating respiratory diseases such as bronchial asthma with less side effects and also of providing a medicament containing the same.

The inventors have further conducted extensive studies on compounds having inhibitory activity upon type IV PDE and, as a result, found that a compound in which a specific substituent (—X—$R^6$) is introduced into the 3-position of the compound previously reported (WO96/06843) is a novel compound and has a strong type IV PDE inhibitory action, as well as excellent oral absorbability and metabolic stability. Therefore, they have found that the compound is markedly useful as a type IV PDE inhibitor, thus resulting in the accomplishment of the invention.

Accordingly, the invention relates to a novel naphthyridine derivative represented by the following general formula (I) or a pharmaceutically acceptable salt thereof and a medicament containing the same as the active ingredient.

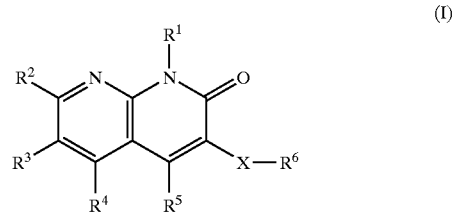

(I)

(wherein each symbol has the following meaning;
$R^1$: —$R^0$, -a lower alkylene-cycloalkyl or -a cycloalkyl
$R^0$: -a lower alkyl,
$R^2$, $R^3$, and $R^4$: —H, —$R^0$, -a halogen, -a lower alkylene-OH, -a lower alkylene-SH, -a lower alkylene-O—$R^0$, -a lower alkylene-S—$R^0$, -a lower alkylene-O—CO—$R^0$, -a lower alkylene-S—CO—$R^0$, —OH, —O—$R^0$, —S—$R^0$, —SO—$R^0$, —$SO_2$—$R^0$, —$NH_2$, —$NHR^0$, —$NR^0_2$, -a cycloalkyl, —CO—$R^0$, or —CH=N—$OR^9$, which may be the same or different from one another,
$R^9$: —H, —$R^0$ or -a lower alkylene-aryl,
$R^5$: a cycloalkyl which may be substituted with a group selected from $R^{10}$, a cycloalkenyl which may be substituted with a group selected from $R^{10}$, a heterocyclic group which may be substituted with a group selected from $R^{10}$, or phenyl which may be substituted with a group selected from $R^{10}$, $R^6$: —OH, —$OR^7$, —COOH, —$COOR^7$, —$CONH_2$, —$CONHR^7$, —$CON(R^7)_2$, —O—$COR^7$, —O—$COOR^7$, —CHO, —$COR^7$, —$NH_2$, —$NHR^7$, —$N(R^7)_2$, —$NHCOR^7$, —$N(R^7)COR^7$, —$NHSO_2R^7$, —$N(R^7)SO_2R^7$, —CN, —$NHCOOR^7$, —$N(R^7)COOR^7$, —$C(NH)NH_2$, —$NHC(NH)NH_2$ or —$N(R_7)C(NH)NH_2$, or a group represented by the formula —Y—$R^8$, $R^7$: a lower alkyl which may be substituted with a group selected from the group consisting of —OH, -phenyl, -a halogen, —$OR^0$, —$CO_2H$, —$CO_2R^0$, —$NH_2$, —$NHR^0$, —$NR^0_2$, —$NO_2$, —CN, and —$COR^0$, $R^8$: a cycloalkyl which may be substituted with a group selected from $R^{10}$, an aryl which may be substituted with a group selected from $R^{10}$, or a heterocyclic group which may be substituted with a group selected from $R^{10}$, $R^{10}$: —OH, -phenyl, -a halogen, —$OR^0$, —$CO_2H$, —$CO_2R^0$, —$NH_2$, —$NHR^0$, —$NR^0_2$, —$NO_2$, —CN or —$COR^0$, or a group described in $R^7$.

Y: a bond, —O—, —COO—, —CONH—, —CON($R^7$)—, —O—CO—, —O—COO—, —CO—, —NH—, —N($R^7$)—, —NHCO—, —N($R^7$)CO—, —NHCOO—, —N($R^7$)COO—, —$NHSO_2$—, or —N($R^7$)$SO_2$—, and X: a bond or a lower alkylene, or a lower alkenylene. The same shall apply hereinafter.).

Also, according to the invention, there is provided a medicament, particularly a type IV PDE inhibitor, which comprises the naphthyridine derivative or a salt thereof.

The following describes the invention in detail.

The term "lower" as used herein means a straight or branched hydrocarbon chain having from 1 to 6 carbon atoms and examples of the "lower alkyl" include methyl, ethyl, propyl, isopropyl, butyl, isobutyl, tert-butyl, pentyl, isopentyl, neopentyl, hexyl, and the like. Preferred is an alkyl having from 1 to 4 carbon atoms, and particularly preferred is methyl or ethyl. The "lower alkylene" means a divalent group formed by removing any one hydrogen atom from the above "lower alkyl" and is preferably an alkylene having from 1 to 4 carbon atoms, particularly preferably methylene, ethylene or propylene. The "lower alkenylene" means a group having one or more double bonds at any position in the "lower alkylene" having two or more carbon atoms, and is preferably an alkenylene having 2 to 4 carbon atoms.

The "cycloalkyl" is preferably a cycloalkyl having from 3 to 8 carbon atoms, particularly preferably cyclopropyl or cyclohexyl. The "cycloalkenyl" is preferably a cycloalkenyl having from 5 to 8 carbon atoms, particularly preferably cyclohexenyl. The "aryl" means an aromatic hydrocarbon group having from 6 to 14 carbon atoms, preferably phenyl. The "heterocyclic group" is a monocyclic to tricyclic heterocyclic group having from 1 to 4 heteroatoms selected from the group consisting of nitrogen atom, oxygen atom, and sulfur atom, which may form a bridged ring or a condensed ring with benzene ring. This heterocycle is preferably a five- to seven-membered saturated or unsaturated monocyclic heterocyclic group, and is particularly preferably pyridine, piperidine, morpholine, thiophene, thiazole, imidazole, tetrazole, pyrazine or piperazine.

The "halogen" means F, Cl, Br or I.

The term "which may be substituted" means "not substituted" or "has from 1 to 5 substituents which may be the same or different from one another".

The substituent in the "cycloalkyl which may be substituted", "cycloalkenyl which may be substituted", "heterocyclic group which may be substituted", "phenyl which may be substituted", and "aryl which may be substituted" is not particularly limited as long as it can used as the substituent of these rings for medicaments, particularly a type IV PDE inhibitor, but is preferably —OH, -phenyl, -a halogen, —$OR^0$, —$CO_2H$, —$CO_2R^0$, —$NH_2$, —$NHR^0$, —$NR^0_2$, —$NO_2$, —CN or —$COR^0$, or a lower alkyl which may be substituted with a group selected from these groups.

The group (X—$R^6$) at the 3-position of the naphthyridine is preferably a group more hydrophilic than the alkyl group having the same carbon atoms. For example, X is preferably a bond or a lower alkylene and $R^6$ is preferably —OH, —COOH, —$COOR^7$, —O—$COR^7$, —$NH_2$, —$NHR^7$, —$N(R^7)_2$, —$C(NH)NH_2$, —$NHC(NH)NH_2$ or —$N(R^7)C(NH)NH_2$, or a group represented by the formula —Y—$R^8$. $R^8$ is preferably an aryl or heterocyclic group. These groups may be substituted with a group selected from the group consisting of —OH, -phenyl, -a halogen, —$OR^0$, —$CO_2H$, —$CO_2R^0$, —$NH_2$, —$NHR^0$, —$NR^0_2$, —$NO_2$, —CN, and —$COR^0$.

The group ($R^5$) at the 4-position of the naphthyridine is preferably a cycloalkyl, phenyl which may have a substituent at the 3-position, or the like. The substituent is preferably a halogen, a lower alkyl, or the like. The groups ($R^3$ and $R^4$) at the 5- and 6-position of the naphthyridine are each preferably a lower alkyl or hydrogen atom, more preferably hydrogen atom. The group ($R^2$) at the 7-position of the naphthyridine is preferably -a lower alkyl, -a halogen, -a lower alkylene-OH, or a group represented by the formula —CH=N—OH.

Among the compounds of the invention, particularly preferable compounds are the following compounds: 3-(2-amidinoethyl)-4-(3-chlorophenyl)-1-ethyl-7-methyl-1,8-naphthyridin-2(1H)-one, 4-(3-chlorophenyl)-1-ethyl-3-(2-guanidinoethyl)-7-methyl-1,8-naphthyridin-2(1H)-one, 4-cyclohexyl-1-ethyl-7-methyl-3-[2-1H-tetrazol-5-yl)ethyl]-1,8-naphthyridin-2(1H)-one, 4-(3-chlorophenyl)-1-ethyl-7-methyl-3-[3-(1H-tetrazol-5-yl)propyl]-1,8-naphthyridin-2(1H)-one, 4-(3-bromophenyl)-1-ethyl-7-methyl-3-[2-1H-tetrazol-5-yl)ethyl]-1,8-naphthyridin-2(1H)-one, 3-[4-(3-chlorophenyl)-1-ethyl-7-methyl-2-oxo-1,2-dihydro-1,8-naphthyridin-3-yl]propanoic acid, 3-(4-cyclohexyl-1-ethyl-7-methyl-2-oxo-1,2-dihydro-1,8-naphthyridin-3-yl)propanoic acid, 3-[4-(3-chlorophenyl)-1-ethyl-7-methyl-2-oxo-1,2-dihydro-1,8-naphthyridin-3-yl]benzoic acid, 3-[4-(3-chlorophenyl)-1-ethyl-7-(hydroxyiminomethyl)-2-oxo-1,2-dihydro-1,8-naphthyridin-3-yl]propanoic acid, 3-[7-chloro-4-(3-chlorophenyl)-1-ethyl-2-oxo-1,2-dihydro-1,8-naphthyridin-3-yl]propanoic acid, 3-[1-ethyl-7-methyl-4-(3-methylphenyl)-2-oxo-1,2-dihydro-1,8-naphthyridin-3-yl]propanoic acid, 4-(3-chlorophenyl)-1-ethyl-7-methyl-3-(piperidin-4-yl)-1,8-naphthyridin-2(1H)-one and 1-{2-[4-(3-chlorophenyl)-1-ethyl-7-methyl-2-oxo-1,2-dihydro-1,8-naphthyridin-3-yl]ethyl}piperidine-4-carboxylic acid, and salts thereof.

Depending on the kinds of substituents, the compounds of the invention may exist in the form of geometrical isomers and tautomers, and isolated forms or mixtures of these isomers are included in the invention.

Also, the compounds of the invention may have asymmetric carbon atoms in some cases, and (R) and (S) forms of optical isomers can exist based on these atoms. The invention includes all of these optical isomers in mixed and isolated forms.

Pharmacologically acceptable prodrugs are also included in the compounds of the invention. The pharmacologically acceptable prodrugs are compounds having groups which can be converted into certain groups of the invention such as $NH_2$, OH and $CO_2H$ by solvolysis or under a physiological condition. Examples of the groups which form prodrugs include those which are described in *Prog. Med.*, 5, 2157–2161 (1985) and "Pharmaceutical Research and Development" (Hirokawa Publishing Co., 1990) Vol. 7 Drug Design 163–198.

The compounds of the invention may form acid addition salts or, depending on the kinds of the substituents, salts with bases. Such salts are pharmaceutically acceptable salts, and their illustrative examples include acid addition salts with inorganic acids such as hydrochloric acid, hydrobromic acid, hydroiodic acid, sulfuric acid, nitric acid and phosphoric acid and organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid and glutamic acid, salts with inorganic bases such as sodium, potassium, magnesium, calcium and aluminum and organic bases such as methylamine, ethylamine, ethanolamine, lysine and ornithine, and ammonium salts.

In addition, the invention also includes various hydrates, solvates and polymorphic substances of the compound (I) of the invention and salts thereof.

(Production Method)

The compound of the invention and pharmaceutically acceptable salts thereof can be produced by applying various known synthetic methods making use of the characteristics based on its fundamental structure or the kind of substituent. In that case, depending on the kind of functional group, it is sometimes effective from the production technical point of view to replace the functional group at the starting material or intermediate stage by an appropriate protecting group, namely a group which can be easily converted into the functional group. Thereafter, the compound of interest can be obtained by removing the protecting group as occasion demands. Hydroxyl group and carboxyl group can be exemplified as such functional groups, and the protecting groups described for example in "Protective Groups in Organic Synthesis (2nd Ed.)" edited by Greene and Wuts can be cited as such protecting groups, which may be optionally used in response to the reaction conditions.

(1) First Production Method

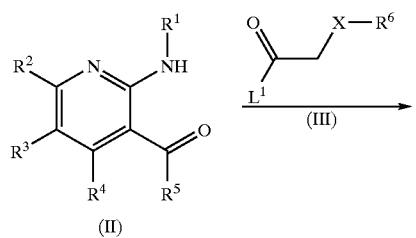

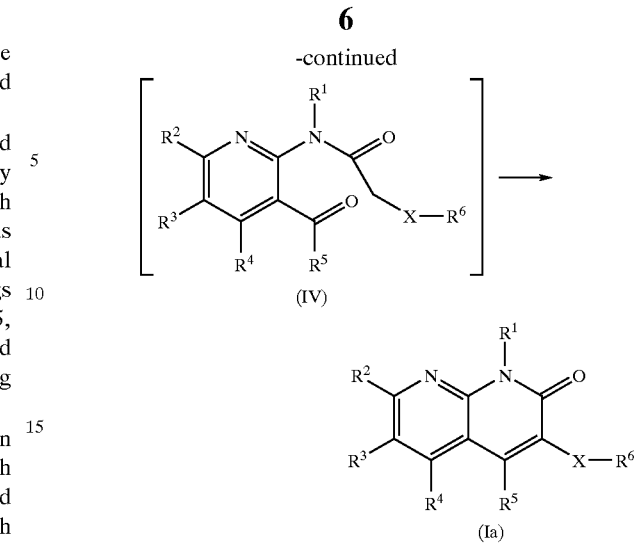

(wherein $L^1$ represents a leaving group. The same shall apply hereinafter.)

In this production method, the compound (Ia) of the invention is produced by reacting an aminopyridine derivative (II) with an acylating agent represented by the general formula (III) to obtain an amide derivative (IV), and then directly subjecting it to a ring-closing reaction.

Preferred examples of the leaving group represented by $L^1$ include halogen atoms, acyloxy, carbonates such as alkyloxycarbonyloxy and organic sulfonic acid residues such as methanesulfonyloxy and p-toluenesulfonyloxy. Also, through the combination of a substituent on $XR^6$ with $L^1$, the general formula (III) may form an intramolecular or intermolecular acid anhydride (e.g., glutaric anhydride).

The reaction is carried out in an organic solvent inert to the reaction, selected from halogenated hydrocarbons such as dichloromethane, dichloroethane and chloroform; aromatic hydrocarbons such as benzene, toluene and xylene; ethers such as diethyl ether, tetrahydrofuran (THF) and dioxane; and N,N-dimethylformamide (DMF); or without solvent, under from cooling to heating. In carrying out the reaction, the aminopyridine derivative (II) and the acylating agent (III) can be used in equivalent amounts or one of them in excess amount, and it is sometimes advantageous for smooth progress of the reaction to carry out the reaction in the presence of an organic base (preferably, triethylamine, pyridine or 4-(N,N-dimethylamino)pyridine), an inorganic base (preferably sodium hydroxide or potassium carbonate) or a metal base (preferably, sodium hydride, sodium methoxide or potassium tert-butoxide).

In this production method, isolation of the amide derivative (IV) and its ring-closing reaction may be carried out stepwise. In that case, with regard to the conditions of solvent, temperature, base and so on, the same conditions as those mentioned above can be employed in each reaction.

(2) Second Production Method

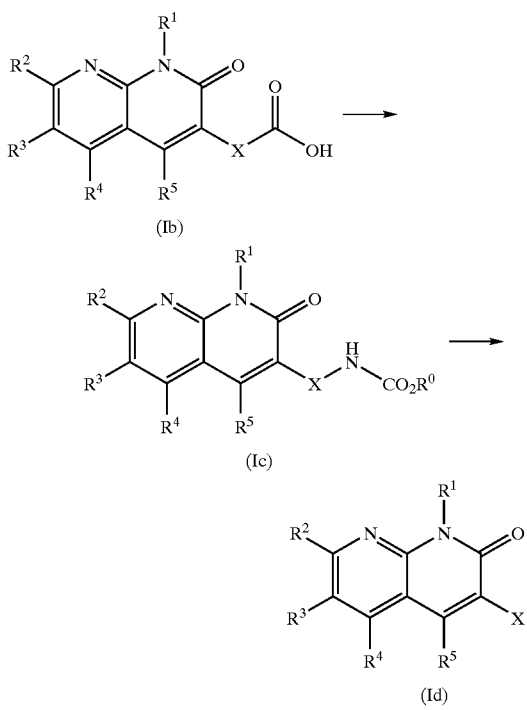

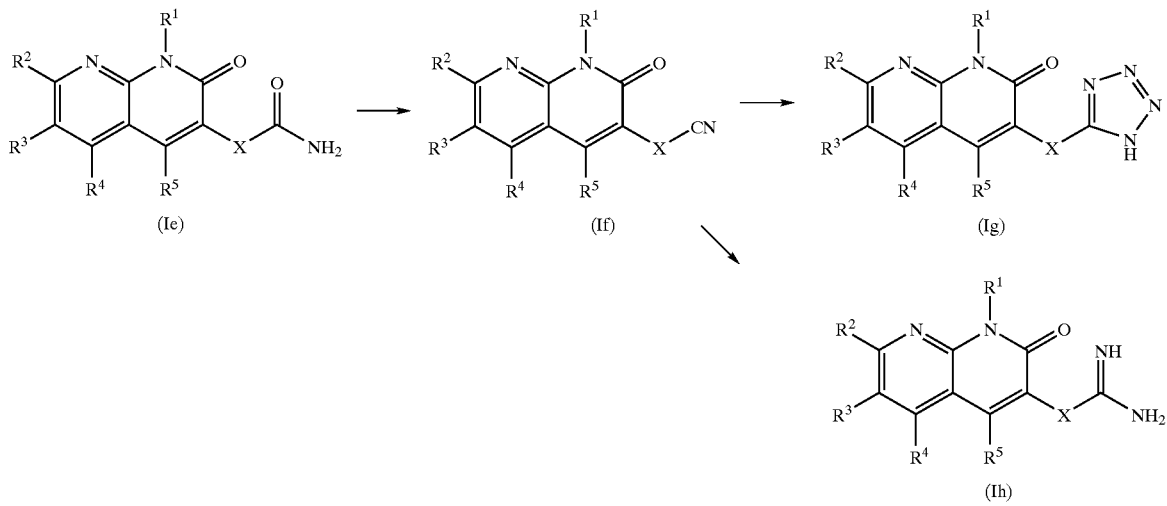

The reaction is carried out in an organic solvent inert to the reaction, selected from halogenated hydrocarbons, aromatic hydrocarbons, ethers and DMF, or without solvent, under from cooling to heating. In carrying out the reaction, the alcohol compound can be used in an equivalent or excess amount based on the compound (Ib).

The compound (Id) of the invention is produced by subjecting the compound (Ic) of the invention to a removing reaction of a carbamate type amino group-protecting group described in the "Protective Groups in Organic Synthesis (2nd Ed.)" mentioned previously. This reaction may be carried out successively without isolating the compound (Ic), following the above reaction.

(3) Third Production Method

A compound having a carboxyl group on $R^8$ of the compound (I) can be produced by hydrolyzing the trifluoromethyl group on $R^8$.

The reaction is carried out in an organic solvent inert to the reaction, selected from halogenated hydrocarbons, aromatic hydrocarbons, ethers and DMF, or without solvent, in the presence of an acid (hydrochloric acid, sulfuric acid, or the like) or a base (sodium hydroxide, sodium methoxide, or the like) under from cooling to heating.

(4) Fourth Production Method

In this production method, a compound (Id) of the invention having amino group is produced from the compound (Ib) of the invention having a carboxyl group. The carbamate compound (Ic) obtainable as the intermediate is also a compound of the invention.

The compound (Ic) of the invention can be produced by reacting an isocyanate compound which is obtained by the Curtius rearrangement of an acid azide obtained by the reaction of a reactive derivative of a carboxyl group obtained from the compound (Ib), such as an acid anhydride, with an azide salt such as sodium azide, or by the diphenylphosphoryl azide (DPPA) method, or which is by Hofmann rearrangement of an primary amide produced from the compound (Ib) according to an conventional amidation reaction, with an alcohol compound.

In this production method, compounds (If), (Ig) and (Ih) of the invention are produced from a compound (Ie) of the invention through the above pathway.

The compound (If) of the invention can be produced by dehydrating the compound (Ie) of the invention. A usual method of dehydration reaction can be used in the reaction, such as a method described for example in "JIKKEN KAGAKU KOZA (4th Ed.)" edited by The Chemical Society of Japan, vol. 20 (1992) (Maruzen).

The compound (Ig) of the invention can be produced by the reaction of the compound (If) of the invention with an azide salt such as sodium azide. The reaction is carried out in a solvent inert to the reaction, selected from halogenated hydrocarbons, aromatic hydrocarbons, ethers, alcohols such as methanol and ethanol, DMF and water, or without solvent, under from cooling to heating. In carrying out the reaction, the azide salt can be used in an equivalent or excess amount based on the compound (If), and it is sometimes advantageous for smoothly progressing the reaction to carry out the reaction in the presence of an acid (acetic acid, trifluoroacetic acid, triethylamine hydrochloride, hydrochloric acid, aluminum chloride or the like) or a base (pyridine, triethylamine, sodium hydroxide, potassium hydroxide, sodium methoxide, potassium tert-butoxide or the like).

The compound (Ih) of the invention can be produced by the reaction of the compound (If) of the invention with ammonia, an ammonium salt such as ammonium chloride or a metal amide such as sodium amide. It can also be produced by allowing an imidoyl chloride obtained by the reaction of the compound (If) with hydrogen chloride to react with an ammonium salt such as ammonium chloride. The reaction is carried out in a solvent inert to the reaction, selected from halogenated hydrocarbons, aromatic hydrocarbons, ethers, alcohols, DMF and water, or without solvent, under from cooling to heating and under from ordinary pressure to a forced pressure. In carrying out the reaction, the amination agent can be used in an equivalent or excess amount based on the compound (If).

(5) Fifth Production Method

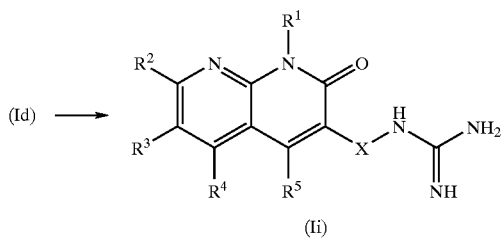

(Ii)

In this production method, a compound (Ii) is produced by a guanidino-forming reaction of the compound (Id) of the invention.

Examples of the guanidino-forming agent to be used in this reaction include cyanamide, amidino sulfate, 1-amidinopyrazole and S-methylisothiourea. The reaction is carried out in a solvent inert to the reaction, selected from halogenated hydrocarbons, aromatic hydrocarbons, ethers, alcohols, DMF and water, or without solvent, under from cooling to heating. In carrying out the reaction, the guanidino-forming agent can be used in an equivalent or excess amount based on the compound (Id), and it is sometimes advantageous for smoothly progressing the reaction to carry out the reaction in the presence of an acid (acetic acid, trifluoroacetic acid, hydrochloric acid, sulfuric acid or the like) or a base (pyridine, dimethylaminopyridine, triethylamine, sodium hydroxide, potassium hydroxide, sodium methoxide, potassium tert-butoxide or the like).

(6) Sixth Production Method

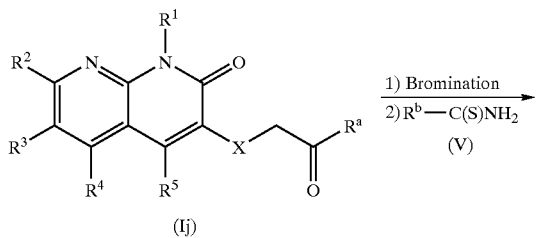

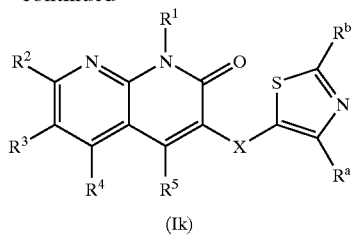

(Ik)

(wherein $R^a$ and $R^b$ may be the same or different and each represents H or a group represented by $R^7$ or $R^8$. The same shall apply hereinafter.)

In this production method, a thiazole derivative (Ik) is produced from the compound (Ij) of the invention.

The aimed compound can be produced by reacting, with a thioamide (V), a bromo compound which is obtained by reacting the compound (Ij) with a brominating agent such as bromine, N-bromosuccinimide, or benzyltrimethylammonium tribromide, after isolation or without isolation. The reaction is carried out in a solvent inert to the reaction, selected from halogenated hydrocarbons, aromatic hydrocarbons, ethers, alcohols, acetic acid, DMF and water, or without solvent, under from cooling to heating. In carrying out the reaction, the compound (Ij) and the brominating agent or the bromo compound and the thioamide (V) can be used in equivalent amounts or one of them in excess amount, and it is sometimes advantageous for smoothly progressing the reaction to carry out the reaction in the presence of an acid or a base.

(7) Seventh Production Method

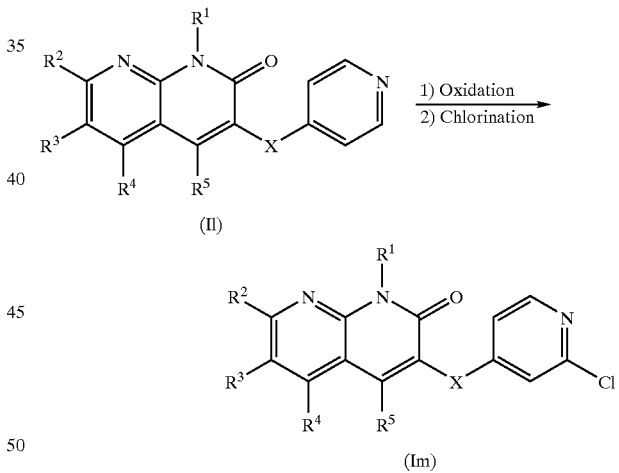

In this production method, a chloro group is introduced into the pyridine ring of the compound (Il) of the invention.

The aimed compound can be produced by reacting a pyridine oxide compound obtainable by reacting the compound (Il) with an oxidating agent such as m-chloroperbenzoic acid, peracetic acid or hydrogen peroxide, with a chlorinating agent such as phosphorus oxychloride, phosphorus pentachloride or thionyl chloride after isolation or without isolation. The reaction is carried out in a solvent inert to the reaction, selected from halogenated hydrocarbons, aromatic hydrocarbons, ethers, alcohols, acetic acid, DMF and water, or without solvent, under from cooling to heating. In carrying out the reaction, the compound (Il) and the oxidating agent or the pyridine oxide compound and the chlorinating agent can be used in equivalent amounts or one of them in excess amount, and it is sometimes advantageous for smoothly progressing the reaction to carry out the reaction in the presence of an acid or a base.

The chloro group can be converted into various substituents by subjecting the compound (Im) of the invention obtained according to the present production method to usual ipso substitution reaction described in the publication of WO97/19078 and so on.

(8) Synthesis of Starting Materials

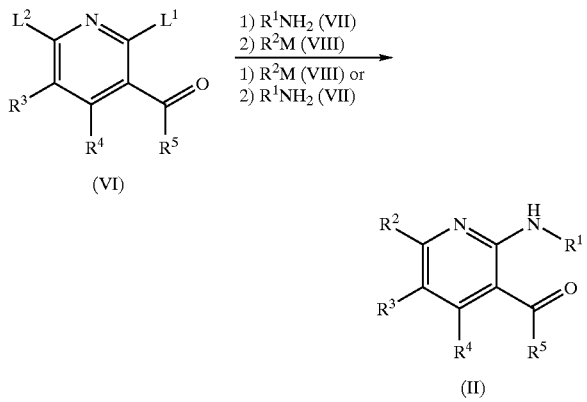

(wherein, $L^2$ represents a leaving group the same as $L^1$ and M represents H or a metal salt. The same shall apply hereinafter.)

A starting compound (II) in which the substituent $R^2$ and the pyridine ring are combined with a carbon-carbon bond and a starting compound (VI) having leaving groups on the 2-position and 6-position of the pyridine ring can be synthesized according to the method described on pages 19 to 21 of the publication of WO97/19078.

A starting compound (II) in which the substituent $R^2$ and the pyridine ring are not combined with a carbon-carbon bond can be synthesized by subjecting the starting compound (VI) to ipso substitution reaction with an amine compound (VII) having $R^1$ group and a nucleophilic reagent $R^2M$ (VIII), successively. The order of the ipso substitution reaction is suitably decided in consideration of the K substituents ($R^1NH$ and $R^2$) and the leaving groups ($L^1$ and $L^2$). The reaction is carried out in a solvent inert to the reaction, selected from water, aromatic hydrocarbons, ethers and DMF, or without solvent, under from cooling to heating. It is sometimes advantageous for smooth progress of the reaction to carry out the reaction in the presence of an organic base, an inorganic base (preferably sodium hydroxide or potassium carbonate) or a metal base.

The compound of the invention obtained by each of the above production methods can be further converted into various compounds of the invention by subjecting the compound to each reaction of amidation, sulfonamidation, esterification, hydrolysis, alkylation, reduction of an ester, or nucleophilic substitution. Amidation, sulfonamidation, and esterification can be carried out according to methods described for example in "JIKKEN KAGAKU KOZA (4th Ed.)" edited by The Chemical Society of Japan, vol. 22 (1992) (Maruzen), hydrolysis according to a method described in the paragraph of deprotection of carboxyl group in the above "Protective Groups in Organic Synthesis (2nd Ed.)", alkylation according to a method described for example in "JIKKEN KAGAKU KOZA (4th Ed.)" edited by The Chemical Society of Japan, vol. 20 (1992) (Maruzen), and reduction of an ester according to a method described for example in "JIKKEN KAGAKU KOZA (4th Ed.)" edited by The Chemical Society of Japan, vol. 20 (1992) (Maruzen). The nucleophilic substitution can be achieved by reacting a compound having an alkyl group substituted with OH with thionyl chloride or the like to form an alkyl chloride derivative or with methanesulfonyl chloride or p-toluenesulfonyl chloride to form an organic sulfonate ester, followed by reaction with a nucleophile. Alternatively, it can be also achieved by carrying out Mitsunobu reaction. The reaction is carried out in an organic solvent inert to the reaction, selected from halogenated hydrocarbons, aromatic hydrocarbons, ethers, and DMF, or without solvent, under from cooling to heating. It is sometimes advantageous for smoothly progressing the reaction to carry out the reaction in the presence of a base.

The reaction product obtained by each of the above production methods is isolated and purified as its free compound, salt or various solvates such as hydrate. The salt can be produced by carrying out a usual salt formation treatment.

The isolation and purification are carried out by employing usually used chemical techniques such as extraction, concentration, evaporation, crystallization, filtration, recrystallization and various types of chromatography.

Various isomers can be isolated in the usual way making use of the difference in physicochemical properties between corresponding isomers. For example, optical isomers can be separated by a general optical resolution method such as a fractional crystallization or chromatography. Also, an optical isomer can be produced starting from an appropriate optically active material compound.

INDUSTRIAL APPLICABILITY

Regarding the PDE inhibitory action, at least five types of from I to V have so far been known, and the compound of the invention has particularly excellent activity to inhibit type IV PDE and is therefore useful as an agent for preventing and/or treating respiratory diseases (e.g., bronchial asthma (including atopic asthma), chronic bronchitis, pneumonic diseases and adult respiratory distress syndrome (ARDS)) in which the type IV PDE participates. Particularly, it can be expected to be an agent for preventing and/or treating bronchial asthma.

In addition, the compound of the invention is also useful as an agent for preventing and/or treating other diseases in which involvement of the type IV PDE is known, such as those in which cytokine (IL-1, IL-4, IL-6 and TNF (tumor necrosis factor)) or the like are concerned (e.g., rheumatoid arthritis, ulcerative colitis, Crohn disease, sepsis, septic shock, endotoxin shock, Gram negative bacterial sepsis, toxic shock syndrome, nephritis, hepatitis, infection (bacterial and viral) and circulatory failure (heart failure, arteriosclerosis, myocardial infarction, stroke, or the like)). Also, since the compound of the invention is hardly metabolized by P450 drug metabolizing enzymes present in liver microsome and shows good oral absorbability and duration, it is useful as a long-acting drug having good pharmacokinetic profiles.

Availability of the compound of the invention was confirmed by the following tests.

Test Example 1. Type IV PDE Inhibitory Activity.

1) A solution containing type IV PDE was purified from rat ventricle muscle in the following manner. The heart excised from a male Wistar rat under ether anesthesia was washed with physiological saline and then the ventricle was separated. The thus separated ventricle was finely cut with scissors and suspended in a buffer A (20 mM Bis-Tris, 50 mM sodium acetate, 2 mM EDTA, 5 mM 2-mercaptoethanol, 2 mM benzamidene, 0.05 mM phenylmethylsulfonyl fluoride, pH 6.5) containing 1% PROTEASE INHIBITOR COCKTAIL For Mammalian Cell Extracts (SIGMA). Thereafter, the cells Were disrupted using Polytron and subjected to ultracentrifugation (100,000 G, 60 minutes, 4° C.) to obtain a soluble fraction.

2) The resulting soluble fraction was applied to a 2.6×10 cm Q-Sepharose column equilibrated with the buffer A. Next, the column was washed with 1,200 ml of the buffer A to remove uncombined protein. The protein combined to the column was eluted using 750 ml of the buffer A containing a linear gradient sodium acetate solution of from 0.05 to 1.00 M, and 110 tubes each containing 7 ml fraction were recovered. The cAMP metabolizing PDE activity of each fraction obtained in the presence or absence of cGMP and calcium/calmodulin was examined. Each fraction which showed cAMP metabolizing activity and received no influence on the cAMP metabolizing activity by the presence of cGMP or calcium/calmodulin was used as a stock solution for the inspection of the type IV PDE inhibitory activity.

3) Each test compound in a predetermined concentration was allowed to undergo 10 minutes of the reaction at 30° C. in a reaction mixture containing 40 mM Tris-HCl (pH 8.0), 5 mM magnesium chloride, 4 mM 2-mercaptoethanol, 1 $\mu$M CAMP, 1 $\mu$Ci/ml [$^3$H] cAMP and the type IV PDE stock solution. The reaction was stopped by adding ½ volume of 20 mg/ml polylysine coated yttrium silicate SPA beads (Amersham) suspension containing 18 mM zinc sulfate and 5 $\mu$M 3-isobutyl-1-methylxanthine (IBMX) to the reaction solution, and the radioactivity was measured.

A concentration of test compound which inhibits 50% of the metabolic activity of type IV PDE was defined as $IC_{50}$ and calculated for each compound.

By applying the above test method and the method described in WO 97/19078, the type I, II, III and V PDE inhibition activities were measured in the same manner.

As a result of the above inhibitory activity measuring test, it was confirmed that the compounds of Examples 2, 16, 21, 28, 38, 39, 40, 41, 43, 47, 61, 70, 77, 78, 79 and 80 have an $IC_{50}$ value of 11 nM or less for the type IV PDE, including a compound having a potent activity of 0.002 nM.

Test Example 2. In vitro Drug Metabolism Test Using Liver Microsome

1) Human and rat liver microsome suspension (human microsome: Xenotech, rat microsome: Charles River) was diluted with 100 mM Na-K phosphate buffer (pH 7.4) to a protein concentration of 0.5 mg/ml. To a 100 $\mu$l portion of this suspension were added 2 $\mu$l of a test compound solution (a 10 $\mu$g/ml acetonitrile solution), 500 $\mu$l of 200 mM Na-K phosphate buffer (pH 7.4), 50 $\mu$l of 1 mM EDTA-NaOH (pH 7.4) and 200 $\mu$l of purified water, thereby preparing a substrate solution (concentration in the reaction solution: liver microsome (as the protein content) 0.05 mg/ml, test compound 20 ng/ml, 100 mM Na-K phosphate buffer, 0.1 mM EDTA-NaOH).

2) An NADPH production system was prepared by mixing 42 mg of NADP, 5 ml of 100 mM glucose-6-phosphatase (G6P) and 5 ml of 100 mM MgCl$_2$, and adding 57 $\mu$l of G6P dehydrogenase (about 1750 U/5 mg/ml) to the mixture. This was heated at 37° C. for 5 minutes and then ice-cooled until its use.

3) A 900 $\mu$l portion of the substrate solution was pre-incubated at 37° C. for 5 minutes, and then 100 $\mu$l of the NADPH production system was added thereto, following by reaction at 37° C. for 10, 20 and 30 minutes. After termination of the reaction by adding 2 ml of ethyl acetate, the whole was ice-cooled. In this connection, a control sample was prepared by adding 100 $\mu$l of the NADPH production system after adding 2 ml of ethyl acetate (0 minute reaction).

4) To the reaction solution was added 100 $\mu$l of an internal standard substance having a predetermined concentration (an acetonitrile solution), 1 ml of 0.5 M phosphoric acid and 2 ml of ethyl acetate, followed by shaking for 10 minutes. After 10 minutes of centrifugation at 2,500 rpm, the ethyl acetate layer was separated and evaporated to dryness, and the residue was dissolved in 100 $\mu$l of an HPLC mobile phase solvent. The test compound was eluted after about 12 minutes, and the internal standard substance after about 16 minutes, under the following conditions. (HPLC measuring conditions mobile phase: acetonitrile/20 mM ammonium acetate=2:3 (v/v), column: Discovery RP Amide C16, 4.6× 35 mm (SUPELCO), flow rate: 0.8 ml/min., detection: UV 286 nm)

5) A ratio (residual ratio) of the peak height ratio after 10, 20 or 30 minutes of the reaction to the peak height ratio of each test compound in the control (peak height ratio to the internal standard substance) was calculated.

As a result of the above measuring test, it was confirmed that the compounds of Examples 2, 21, 28, 41, 43, 47, 77 and 79 are hardly metabolized by the P450 drug metabolizing enzyme present in the liver microsome. Test Example 3. Oral absorbability and pharmacokinetic profile evaluation test using type IV PDE inhibitory activity as the index The following assay was carried out in order to evaluate oral absorbability and pharmacokinetic profiles of the type IV PDE-inhibiting compounds of the invention.

1) Each test compound suspended in purified water containing 0.5% methyl cellulose was orally administered to a seven-week-old male Fisher rat at a dose of 3 mg/kg. In the control group, a solvent (0.5% methyl cellulose in purified water, 3 ml/kg) was administered in the same manner. After the oral administration, blood samples were periodically collected in the presence of heparin from the caudal vein of each rat under ether anesthesia, and plasma was prepared in the usual way.

2) The plasma prepared from each rat administered with the test compound or solvent was added to the type IV PDE measuring system shown in the above Test Example 1 so as to be a final concentration of 0.1%, and the type IV PDE inhibitory activity was measured.

As a result of this test, it was revealed that the compounds of Examples 2, 21, 28, 41, 43, 47, 77 and 79 show good oral absorbability and metabolic stability in comparison with a comparative compound. (Comparative compound: 4-(3-chlorophenyl)-1-ethyl-7-methyl-2-oxo-1,2-dihydro-1,8-naphthyridine)

Based on the results of Test Examples 1 to 3, it was confirmed that the compound of the invention has type IV PDE inhibitory activity, and thus it is evident that it is useful as an agent for preventing and treating diseases in which the type IV PDE participates.

The pharmaceutical composition containing one or two or more of the compounds of the invention or salts thereof as the active ingredient is prepared using carriers, excipients and other additives which are generally used in the preparation of medicaments.

The administration may be either oral administration in the form of, e.g., tablets, pills, capsules, granules, powders or liquids or parenteral administration in the form of, e.g., intravenous or intramuscular injections, suppositories, transdermal preparations, transnasal preparations or inhalations. The dose is optionally decided in response to each case, e.g., by taking symptoms, age and sex of each patient to be treated into consideration, but is usually approximately from 0.001 mg/kg to 100 mg/kg per day per adult in the case of oral administration, which is administered once a day or by dividing into 2 to 4 doses per day. Also, when intravenous administration is conducted due to the symptoms, it is administered once or several times a day generally within the range of from 0.001 mg/kg to 10 mg/kg per day per adult. Also, in the case of inhalation, it is administered once or several times a day generally within the range of from 0.0001 mg/kg to 1 mg/kg per day per adult, and in the case of spreading, it is administered once or several times a day within the range of from 0.0001 mg/kg to 1 mg/kg per day per adult.

The solid composition in the oral administration according to the invention is used in the form of, e.g., tablets, powders or granules. In such a solid composition, one or more active substances are mixed with at least one inert filler such as lactose, mannitol, glucose, hydroxypropylcellulose, microcrystalline cellulose, starch, polyvinylpyrrolidone or aluminum magnesium silicate. In the usual way, the composition may contain inert additives including a lubricant such as magnesium stearate and a disintegrating agent such as carboxymethylstarch sodium or a solubilization assisting agent. If necessary, tablets or pills may be coated with a film of sugar or a gastric or enteric coating substance.

The liquid composition for oral administration contains, e.g., pharmaceutically acceptable emulsions, liquids, suspensions, syrups and elixirs and contains a generally used inert solvent such as purified water or ethanol. In addition to the inert solvent, this composition may also contain auxiliary agents such as a solubilizing agent, a moistening agent and a suspending agent, as well as sweeteners, flavors, aromatics and antiseptics.

The injections for parenteral administration use include aseptic aqueous or non-aqueous liquids, suspensions and emulsions. Examples of the aqueous solvent include distilled water for injection and physiological saline. Examples of the non-aqueous solvent include propylene glycol, polyethylene glycol, a plant oil such as olive oil, an alcohol such as ethanol, and polysorbate 80 (trade name). Such a composition may further contain a tonicity agent, an antiseptic, a moistening agent, an emulsifying agent, a dispersing agent, a stabilizing agent and a solubilization assisting agent. These compositions are sterilized, e.g., by filtration through a bacteria retaining filter, blending of a germicide or irradiation. In addition, these may be used by firstly making into sterile solid compositions and dissolving them in sterile water or a sterile solvent for injection use prior to their use.

BEST MODE FOR CARRYING OUT THE INVENTION

The invention is illustratively described with reference to the following Examples which, however, do not limit the scope of the invention. Methods for producing the starting compounds are shown in the following Reference Examples. In this connection, 3-(3-chlorobenzoyl)-2-ethylamino-6-dimethoxymethylpyridine was produced in accordance with the method described in Reference Examples 44 of the publication of WO 97/19078, and 3-substituted 2-ethylamino-6-methylpyridine derivatives such as 3-(3-chlorobenzoyl)-2-ethylamino-6-methylpyridine and 3-cyclohexanecarbonyl-2-ethylamino-6-methylpyridine were produced in accordance with the methods described in Reference Examples 45, 48 and 51 of the publication of WO 97/19078, respectively.

The following abbreviations are used in Reference Examples and the following Tables. Ex: Example number, No: Compound number, Dat: physicochemical data (MS: FAB-MS (M+H)$^+$, MP: melting point (° C.), dec: decomposition, NMR1: δ (ppm) of characteristic peaks of $^1$H-NMR in CDCl$_3$, NMR2: δ (ppm) of characteristic peaks of $^1$H-NMR in DMSO-d$_6$), Sal: salt and contained solvent (oxa: oxalate, fum: fumarate, blank column: free compound, the numeral before a component, for example, 1 HCl means monohydrochloride), Syn: production method (each numeral indicates a similarly produced Example number), Me: methyl, Et: ethyl, cPr: cyclopropyl, cHex: cyclohexyl, Ph: phenyl, Ac: acetyl, Py2: pyridin-2-yl, and Py4: pyridin-4-yl. In addition, the numeral before each substituent shows the position of substitution, for example, 2-Cl-Py4 means 2-chloropyridin-4-yl and 3-Cl-Ph means 3-chlorophenyl.

Reference Example 1

A DMF solution of 3-(3-chlorobenzoyl)-2-ethylamino-6-methylpyridine was treated with 60% sodium hydride and then reacted with monoethyl chloroglutarate under heating. Thereafter, the whole was worked up and purified in a usual manner to obtain ethyl 4-{N-[3-(3-chlorobenzoyl)-6-methylpyridin-2-yl]-N-ethylcarbamoyl}butanoate. The resulting compound was reacted with sodium methoxide in ethanol under heating, then concentrated sulfuric acid was added to the reaction mixture, followed by reaction under heating for 2 days. Thereafter, the reaction mixture was worked up and purified in a usual manner to obtain ethyl 3-[4-(3-chlorophenyl)-1-ethyl-7-methyl-2-oxo-1,2-dihydro-1,8-naphthyridin-3-yl]propanoate. MS: 399.

Reference Example 2

In a similar manner to Reference Example 1, ethyl [4(3-chlorophenyl)-1-ethyl-7-methyl-2-oxo-1,2-dihydro-1,8-naphthyridin-3-yl]acetate was obtained. NMR1: 6.91 (1H, d, J=8.1 Hz), 4.13 (2H, q, J=7.1 Hz), 3.43 (2H, s).

Reference Example 3

In a similar manner to Reference Example 1, methyl 4-[4-(3-chlorophenyl)-1-ethyl-7-methyl-2-oxo-1,2-dihydro-1,8-inaphthyridin-3-yl]butanoate was obtained. NMR1: 6.88 (1H, d, J=7.8 Hz), 4.67 (2H, q, J=7.0 Hz), 2.27 (2H, t, J=7.6 Hz).

Reference Example 4

After the reaction of 3-(3-chlorobenzoyl)-2-ethylamino-6-methylpyridine with isochroman-1,3-dione (75%) under heating, the compound obtained by usual work-up was reacted with methyl iodide in 2-butanone in the presence of potassium carbonate. Thereafter, the reaction mixture was worked up and purified in a usual manner to obtain methyl 2-[4-(3-chlorophenyl)-1-ethyl-7-methyl-2-oxo-1,2-dihydro-1,8-naphthyridin-3-yl]benzoate as a yellow solid. MS: 433.

Reference Example 5

After the treatment of 4-cyanobutanoic acid with sodium methoxide in methanol, the treated compound was reacted with pivaloyl chloride in THF. Thus obtained compound was reacted with 3-(3-chlorobenzoyl)-2-ethylamino-6-methylpyridine under heating. Then, the compound obtained by usual work-up was reacted in ethanol in the presence of sodium methoxide under heating. Thereafter, the reaction mixture was worked up and purified in a usual manner to obtain 4-(3-chlorophenyl)-3-(2-cyanoethyl)-1-ethyl-7-methyl-1,8-naphthyridin-2(1H)-one as a pale yellow solid. MS: 352.

Reference Example 6

A compound obtained by reacting 3'-trifluoromethylphenylacetic acid with pivaloyl chloride in THF in the presence of triethylamine was stirred, with the addition of 3-(3-chlorobenzoyl)-2-ethylamino-6-methylpyridine, at 150° C. for 15 hours. Thereafter, the reaction mixture was worked up and purified in a usual manner to obtain 4-(3-chlorophenyl)-1-ethyl-7-methyl-3-(3-trifluoromethylphenyl)-1,8-naphthyridin-2(1H)-one as a colorless solid. MS: 443

Reference Example 7

In a similar manner to Reference Example 6, 4-(3-chlorophenyl)-1-ethyl-7-methyl-3-(4-trifluoromethylphenyl)-1,8-naphthyridin-2(1H)-one was obtained. MS: 443

Reference Example 8

Ethyl 2-(2-aminothiazol-4-yl)acetate was reacted with acetyl chloride in dichloroethane in the presence of triethylamine, and then the reaction mixture was worked up and purified in a usual manner to obtain ethyl 2-(2-acetylaminothiazol-4-yl)acetate as a colorless solid. MS: 229.

Reference Example 9

Ethyl 2-(2-acetylaminothiazol-4-yl)acetate was reacted in a mixture of ethanol-1M sodium hydroxide aqueous solution (1:1) at room temperature, and then the reaction mixture was worked up and purified in a usual manner to obtain 2-(2-acetylaminothiazol-4-yl)acetic acid as a colorless solid. MS: 201.

Reference Example 10

Using 2-(2-acetylaminothiazol-4-yl)acetic acid, N-{4-[4-(3-chlorophenyl)-1-ethyl-7-methyl-2-oxo-1,2-dihydro-1,8-naphthyridin-3-yl]thiazol-2-yl}acetamide was obtained in a similar manner to Reference Example 6. MS: 439.

Reference Example 11

Ethyl isonipecotate was reacted with benzyl bromoacetate in acetonitrile in the presence of cesium carbonate, and then the reaction mixture was worked up and purified in a usual manner to obtain ethyl 1-(benzyloxycarbonylmethyl)isonipecotate as a colorless oily substance. MS: 306.

Reference Example 12

Ethyl 1-(benzyloxycarbonylmethyl)isonipecotate was subjected to catalytic reduction under a hydrogen atmosphere of 1 atm in ethanol in the presence of 10% palladium-carbon. The resulting compound was treated with sodium methoxide in ethanol and then reacted with pivaloyl chloride in THF. The resulting compound was reacted with 3-(3-chlorobenzoyl)-2-ethylamino-6-methylpyridine under heating, and further treated with sodium methoxide in ethanol. Thereafter, the reaction mixture was worked up and purified in a usual manner to obtain ethyl 1-[4-(3-chlorophenyl)-1-ethyl-7-methyl-2-oxo-1,2-dihydro-1,8-naphthyridin-3-yl]piperidin-4-carboxylate as a yellow oily substance. MS: 454.

Reference Example 13

A THF solution of diisopropylamine was treated with 1.6M butyl]ithium/hexane solution. Thereafter, 2,6-dichloropyridine was added dropwise thereto together with THF and reacted, and then 3-chlorobenzaldehyde was further added dropwise. The reaction mixture was worked up and purified in a usual manner and the resulting compound was reacted with manganese dioxide in toluene under heating. The reaction mixture was worked up and purified in a usual manner to obtain 3-(3-chlorobenzoyl)-2,6-dichloropyridine. MS: 286.

Reference Example 14

To a THF solution of 2,6-dichloro-3-(3-chlorobenzoyl)pyridine was added a 70% ethylamine aqueous solution, followed by reaction at room temperature. Thereafter, the reaction mixture was worked up and purified in a usual manner to obtain 6-chloro-3-(3-chlorobenzoyl)-2-ethylaminopyridine. NMR1: 8.95 (1H, brs), 6.48 (1H, d, J=7.8 Hz), 1.31 (3H, t, J=7.1 Hz).

Reference Example 15

Glutaric anhydride and 6-chloro-3-(3-chlorobenzoyl)-2-ethylaminopyridine were reacted under heating at 150° C. and then worked up in a usual manner. The resulting compound was reacted with methyl iodide in 2-butanone in the presence of potassium carbonate at 60° C. Thereafter, the reaction mixture was worked up and purified in a usual manner to obtain methyl 3-[7-chloro-4-(3-chlorophenyl)-1-ethyl-2-oxo-1,2-dihydro-1,8-naphthyridin-3-yl]propanoate as a colorless solid. MS: 405.

Reference Example 16

In DMF was treated 3-(3-chlorobenzoyl)-2-ethylamino-6-dimethoxymethylpyridine with 60% sodium hydride, followed by the reaction with monoethyl chloroglutarate. Thereafter, the reaction mixture was worked up and purified in a usual manner. The resulting compound was reacted in ethanol in the presence of sodium methoxide under heating, and the reaction mixture was worked up and purified in a usual manner. Then, the resulting compound was reacted in a solution of 6M hydrochloric acid-dioxane (1:1) under heating, and then the reaction mixture was worked up and purified in a usual manner. The resulting compound was further reacted with methyl iodide in DMF in the presence of potassium carbonate, and then the reaction mixture was worked up and purified in a usual manner to obtain methyl 3-[4-(3-chlorophenyl)-1-ethyl-7-formyl-2-oxo-1,2-dihydro-1,8-naphthyridin-3-yl]propanoate. NMR1: 10.11 (1H, d, J=0.6 Hz), 2.45–2.95 (4H, m), 1.43 (3H, t, J=7.1 Hz).

Reference Example 17

A 15% sodium thiomethoxide aqueous solution was added dropwise to a DMF solution of 2,6-dichloro-3-(3-chlorobenzoyl)pyridine under ice cooling. After reaction, the reaction mixture was worked up and purified in a usual manner. The resulting compound was reacted with a 70% ethylamine aqueous solution in a sealed tube under heating at 110° C. Thereafter, the reaction mixture was worked up and purified in a usual manner to obtain 3-(3-chlorobenzoyl)-2-ethylamino-6-methylsulfanylpyridine. NMR1: 6.36 (1H, dd, J=8.2, 0.7 Hz), 2.58 (3H, s), 1.32 (3H, t, J=7.1 Hz).

Reference Example 18

To a dichloromethane solution of 4-(3-chlorophenyl)-1-ethyl-7-methyl-3-(pyridin-4-yl)-1,8-naphthyridin-2(1H)-one was added m-chloroperbenzoic acid at room temperature, followed by stirring for 5 hours. Thereafter, the reaction mixture was worked up and purified in a usual manner to obtain 4-(3-chlorophenyl)-1-ethyl-7-methyl-3-(1-oxypyridine-4-yl)-1,8-naphthyridin-2(1H)-one as a colorless solid. MS: 392.

Reference Example 19

To a DMF solution of 3-(3-chlorobenzoyl)-2-ethylamino-6-methylpyridine were added chloroacetyl chloride and pyridine, followed by reaction at room temperature. Thereafter, the whole was worked up and purified in a usual manner to obtain N-[3-(3-chlorobenzoyl)-6-methylpyridin-2-yl]—N-ethylchloroacetamide. To an acetonitrile solution of the compound were added N-tert-butoxycarbonylpiperazine and potassium carbonate, followed by reaction under heating. Thereafter, the reaction mixture was worked up and purified in a usual manner to obtain 2-[4-tert-butoxycarbonylpiperazin-1-yl]—N-[3-(3-chlorobenzoyl)-6-methylpyridin-2-yl]-N-ethylacetamide. The resulting compound was reacted with sodium methoxide in methanol under heating. Thereafter, the reaction mixture was worked up and purified in a usual manner to obtain 3-(1-tert-butoxycarbonylpiperazin-4-yl)-4-(3-chlorophenyl)-1-ethyl-7-methyl-1,8-naphthyridin-2(1H)-one. NMR1: 4.73 (2H, q, J=7.3 Hz), 3.15–3.35 (2H, m), 1.38 (9H, s).

Reference Example 20

To a THF solution of 4-(3-chlorophenyl)-1-ethyl-3-(3-hydroxypropyl)-7-methyl-1,8-naphthyridin-2(1H)-one were added triethylamine and methanesulfonyl chloride, followed by reaction under heating. Thereafter, the reaction mixture was worked up and purified in a usual manner to obtain 4-(3-chlorophenyl)-1-ethyl-3(3-methanesulfonyloxypropyl)-7-methyl-1,8-naphthyridin-2(1H)-one. NMR1: 4.67 (2H, q, J=7.1 Hz), 4.18 (2H, t, J=6.3 Hz), 2.93 (3H, s).

Reference Example 21

To a THF solution of 4-[4-(3-chlorophenyl)-1-ethyl-7-methyl-2-oxo-1,2-dihydro-1,8-naphthyridin-3-yl]butanoic acid were added oxalyl chloride and one drop of DMF, followed by stirring at room temperature. The reaction mixture was added dropwise to an ice-cooled THF solution of concentrated aqueous ammonia and then, the whole was stirred for 30 minutes. Thereafter, the reaction mixture was worked up and purified in a usual manner to obtain 4-[4-(3-chlorophenyl)-1-ethyl-7-methyl-2-oxo-1,2-dihydro-1,8-naphthyridin-3-yl]butanamide. To a dichloroethane solution of the resulting compound were added pyridine, phosphorus oxychloride and one drop of DMF, followed by stirring at room temperature. Thereafter, the reaction mixture was worked up and purified in a usual manner to obtain 4-(3-chlorophenyl)-3-(3-cyanopropyl)-1-ethyl-7-methyl-1,8-naphthyridin-2(1H)-one. NMR1: 6.90 (1H, d, J=8.2 Hz), 4.67 (2H, q, J=7.1 Hz), 1.70–2.10 (2H, m).

Reference Example 22

To a diethyl ether suspension of magnesium was added dropwise 2-bromothiophene at room temperature, and the whole was reacted. After cooling to 0° C., the reaction mixture was added with 2-chloro-6-methylnicotinic acid and, after being warmed to room temperature, the whole was stirred for 12 hours. Thereafter, the reaction mixture was worked up and purified in a usual manner to obtain 2-chloro-6-methyl-3-(thiophene-2-carbonyl)pyridine. NMR1: 7.79 (1H, dd, J=5.0, 1.1 Hz), 7.78 (1H, d, J=7.7 Hz), 2.63 (3H, s).

Reference Example 23

In a sealed tube were heated and stirred 2-chloro-6-methyl-3-(thiophene-2-carbonyl)pyridine and a 70% ethylamine aqueous solution. Thereafter, the reaction mixture was worked up and purified in a usual manner to obtain 2-ethylamino-6-methyl-3-(thiophene-2-carbonyl)pyridine. NMR1: 7.97 (1H, d, J=8.1 Hz), 7.62 (1H, dd, J=5.0, 1.1 Hz), 1.28 (3H, t, J=7.3 Hz).

Reference Example 24

A DMF solution of 3-(3-chlorobenzoyl)-6-dimethoxymethyl-2-ethylaminopyridine was treated with sodium hydride at 0° C. and then monoethyl chloroglutarate was added thereto, followed by heating at 80° C. under stirring. Thereafter, the reaction mixture was worked up in a usual manner. The resulting compound was dissolved in ethanol and sodium methoxide was added thereto at 0° C., followed by heating under reflux for 1 hour. The reaction mixture was cooled to 0° C. and then concentrated sulfuric acid was added thereto, followed by heating under reflux for 1 hour. Thereafter, the reaction mixture was worked up in a usual manner. The resulting compound was dissolved in dioxane and 6M hydrochloric acid was added thereto at 0° C. and, after being warmed to room temperature, the whole was stirred for 3 hours. Thereafter, the reaction mixture was worked up in a usual manner to obtain 3-[4-(3-chlorophenyl)-1-ethyl-7-formyl-2-oxo-1,2-dihydro-1,8-naphthyridin-3-yl]propanoic acid. NMR1: 10.12 (1H, s), 7.70 (1H, d, J=8.1 Hz), 1.44 (3H, t, J=6.9 Hz).

Reference Example 25

To an acetone solution of 3-(3-chlorobenzoyl)-6-dimethoxymethyl-2-ethylaminopyridine was added 6M hydrochloric acid, and the whole was reacted at room temperature for 5 hours. After removal of the solvent by evaporation, propylene oxide and chloroacetyl chloride were added to the product obtained by a usual liquid-separation treatment in methyl t-butyl ether, and the whole was stirred at 60° C. for 14 hours. Thereafter, the reaction mixture was worked up and purified in a usual manner to obtain 2-chloro-N-[3-(3-chlorobenzoyl)-6-formylpyridin-2-yl]-N-ethylacetamide as a yellow oily substance. NMR1: 10.1 (1H, d, J=0.6 Hz), 7.95 (2H, brs), 1.0–1.5 (3H, m).

Reference Example 26

To an acetonitrile solution of 2-chloro-N-[3-(3-chlorobenzoyl)-6-formylpyridin-2-yl]-N-ethylacetamide were added cesium carbonate and ethyl isonipecotate, followed by stirring at 60° C. for 3 hours. After inorganic matter was removed by filtration and the solvent was evaporated, the resulting residue was dissolved in ethanol, sodium methoxide was added thereto, followed by heating under reflux for 15 minutes. Thereafter, the reaction mixture was worked up and purified in a usual manner to obtain ethyl 1-[4-(3-chlorophenyl)-1-ethyl-7-formyl-2-oxo-1,2-k dihydro-1,8-naphthyridin-3-yl]piperidine-4-carboxylate as a yellow oily substance. MS: 468.

Reference Example 27

To an ethanol solution of ethyl 1-[4-(3-chlorophenyl)-1-ethyl-7-formyl-2-oxo-1,2-dihydro-1,8-naphthyridin-3-yl]piperidine-4-carboxylate was added sodium borohydride under ice cooling, followed by stirring for 15 minutes. Thereafter, the reaction mixture was worked up and purified in a usual manner to obtain ethyl 1-[4-(3-chlorophenyl)-1-ethyl-7-hydroxymethyl-2-oxo-1,2-dihydro-1,8-naphthyridin-3-yl]piperidine-4-carboxylate as a yellow oily substance. MS: 470.

Reference Example 28

To a THF solution of (l-acetylpiperidin-4-yl)acetic acid were added under room temperature triethylamine and pivaloyl chloride, followed by stirring at room temperature for 1 hour. The reaction mixture was filtered and concentrated. Then, 3-cyclohexanecarbonyl-2-ethylamino-6-methylpyridine was added to the residue, followed by stirring at 150° C. for 14 hours. Ethanol and sodium methoxide were added to the product obtained by working up the reaction mixture, and the whole was heated under reflux for 1 hour. Thereafter, the reaction mixture was worked up and purified in a usual manner to obtain 3-(1-acetylpyridin-4-yl)-4-cyclohexyl-1-ethyl-7-methyl-1,8-naphthyridin-2(1H)-one as a colorless solid. MS: 396.

Reference Example 29

To a dichloroethane solution of 3-(3-bromobenzoyl)-2-ethylamino-6-methylpyridine were added p-toluenesulfonyl chloride, (1-ethoxycarbonylpiperidin-4-yl)acetic acid and 4-dimethylaminopyridine, followed by stirring at 80° C. for 12 hours. Ethanol and sodium methoxide were added to the product obtained by working up the reaction mixture, and the whole was heated under reflux for 1 hour. Thereafter, the reaction mixture was worked up and purified in a usual manner to obtain 4-(3-bromophenyl)-3-(1-ethoxycarbonylpiperidin-4-yl)-1-ethyl-7-methyl-1,8-naphthyridin-2(1H)-one as a pale brown solid. MS: 498.

Reference Example 30

4-(3-Bromophenyl)-3-(2-cyanoethyl)-1-ethyl-7-methyl-1,8-naphthyridin-2(1H)-one was synthesized in a similar manner to Reference Example 5. MS: 396.

Reference Example 31

4-Cyclohexyl-3-(2-cyanoethyl)-1-ethyl-7-methyl-1,8-naphthyridin-2(1H)-one was synthesized in a similar manner to Reference Example 5. MS: 324.

Reference Example 32

4-(3-Chlorophenyl)-1-ethyl-3-(2-hydroxyethyl)-7-methyl-1,8-naphthyridin-2(1H)-one was obtained in a similar manner to the following Example 16. NMR1: 6.92 (1H, d, J=8.2 Hz), 4.67 (2H, q, J=7.0 Hz), 3.74 (2H, t, J=5.8 Hz).

Reference Example 33

5-(3-Chlorophenyl)-8-ethyl-6-[3-(morpholin-4-yl)-3-oxopropyl]-7-oxo-7,8-dihydro-1,8-naphthyridine-2-carbaldehyde was synthesized in a similar manner to the following Example 6. NMR1: 7.69 (1H, d, J=8.1 Hz), 3.51–3.67 (BH, m), 1.44 (3H, t, J=7.0 Hz).

EXAMPLE 1

To a 50 ml dichloroethane solution containing 7.5 g of 3-(3-chlorobenzoyl)-2-ethylamino-6-methylpyridine were added 5 ml of monoethyl chloromalonate and 6.5 g of 4-dimethylaminopyridine. The whole was stirred at room temperature for 30 minutes, and then further under heating at an oil bath temperature of 80° C. for 30 minutes. The reaction mixture was cooled to room temperature and, after adding 1M hydrochloric acid, extracted with chloroform. The organic layer was washed with saturated brine and then the solvent was evaporated. The resulting residue was purified by a silica gel column chromatography (hexane-ethyl acetate to chloroform-ethyl acetate) to obtain 7.10 g of ethyl 4-(3-chlorophenyl)-1-ethyl-7-methyl-2-oxo-1,2-dihydro-1,8-naphthyridin-3-carboxylate as colorless crystals.

EXAMPLE 2

A 15 ml portion of a 1M sodium hydroxide aqueous solution was added to 15 ml of a THF-methanol (1:1) solution containing 2.70 g of ethyl 3-[4-(3-chlorophenyl)-1-ethyl-7-methyl-2-oxo-1,2-dihydro-1,8-naphthyridin-3-yl]propanoate, followed by stirring under heating at an oil bath temperature of 80° C. for 2 hours. After cooling to room temperature, the whole was adjusted to pH 3 with 1M hydrochloric acid and extracted with ethyl acetate. The organic layer was washed with saturated brine and then the solvent was evaporated. The resulting residue was purified by a silica gel column chromatography (chloroform-methanol) and further recrystallized from diisopropyl ether-ethyl acetate to obtain 1.27 g of 3-[4-(3-chlorophenyl)-1-ethyl-7-methyl-2-oxo-1,2-dihydro-1,8-naphthyridin-3-yl]propanoic acid as colorless crystals.

EXAMPLE 3

A mixture of 1.00 g of 3-(3-chlorobenzoyl)-2-ethylamino-6-methylpyridine and 5.17 g of 2,2-dimethylglutraric anhydride was stirred at 200° C. for 1.5 days. The reaction mixture was cooled to room temperature and, after adding 0.5M hydrochloric acid, heated under reflux for 2 hours. Then, the reaction mixture was cooled to room temperature and extracted with ethyl acetate. The organic layer was washed with saturated brine and then the solvent was evaporated. The resulting residue was purified by a silica gel column chromatography (hexane-ethyl acetate) and then recrystallized from ethanol-water to obtain 198 mg of 3-[4-(3-chlorophenyl)-1-ethyl-7-methyl-2-oxo-1,2-dihydro-1,8-naphthyridin-3-yl]-2,2-dimethylpropanoic acid as orange crystals.

EXAMPLE 4

A 10 ml portion of polyphosphoric acid was added to 320 mg of 4-(3-chlorophenyl)-3-cyano-1-ethyl-1,8-naphthyridin-2(1H)-one, followed by stirring under heating at an oil bath temperature of 130° C. for 2 hours. The reaction mixture was poured into ice-water, adjusted to about pH 6 with a 1M sodium hydroxide aqueous solution and extracted with chloroform. The organic layer was washed with saturated brine and then the solvent was evaporated. The resulting residue was purified by a silica gel column chromatography (chloroform-ethyl acetate) and then recrystallized from ethanol to obtain 180 mg of 4-(3-chlorophenyl)-1-ethyl-7-methyl-2-oxo-1,2-dihydro-1,8-naphthyridin-3-carboxamide as colorless crystals.

EXAMPLE 5

A 0.3 ml portion of oxalyl chloride and one drop of DMF were added to a 20 ml THF solution containing 1.00 g of 3-[4-(3-chlorophenyl)-l-ethyl-7-methyl-2-oxo-1,2-dihydro-1,8-naphthyridin-3-yl]propanoic acid, followed by stirring at room temperature for further 30 minutes. The reaction mixture was added dropwise to an ice-cooled 10 ml THF solution containing 1.0 ml of morpholine, followed by stirring for 30 minutes. To the reaction mixture was added 1M hydrochloric acid and the whole was extracted with ethyl acetate. The organic layer was washed with water and saturated brine and then the solvent was evaporated. The resulting residue was purified by a silica gel column chromatography (chloroform-methanol) and then recrystallized from diisopropyl ether-ethyl acetate to obtain 780 mg of 4-(3-chlorophenyl)-1-ethyl-7-methyl-3-[3-(morpholin-4-yl)-3-oxopropyl]-1,8-naphthyridin-2(1H)-one as colorless crystals.

EXAMPLE 6

Under ice cooling, 630 mg of 1-ethyl-3-(3-dimethylaminopropyl)carbodiimide hydrochloride, 154 mg of dimethylamine hydrochloride and 0.53 ml of triethylamine were added successively to a 10 ml DMF solution containing 700 mg of 3-[4-(3-chlorophenyl)-1-ethyl-7-methyl-2-oxo-1,2-dihydro-1,8-naphthyridin-3-yl]propanoic acid. The reaction mixture was warmed to room temperature and stirred for 2 hours. The reaction mixture was diluted with water and extracted with ethyl acetate. The organic layer was washed with saturated brine and then the solvent was evaporated. The residue was purified by a silica gel column chromatography (chloroform-ethyl acetate) and then recrystallized from diisopropyl ether to obtain 262 mg of 3-[4-(3-chlorophenyl)-1-ethyl-7-methyl-2-oxo-1,2-dihydro-1,8-naphthyridin-3-yl]-N,N-dimethylpropanamide as colorless crystals.

EXAMPLE 9

To a 10 ml toluene solution containing 1.00 g of 4-(3-chlorophenyl)-1-ethyl-7-methyl-2-oxo-1,2-dihydro-1,8-naphthyridin-3-carboxylic acid were added 900 mg of DPPA and 0.5 ml of triethylamine, followed by heating at an oil bath temperature of 100° C. for 1 hour. Then, 10 ml of ethanol was added thereto and the whole was further stirred under heating for 30 minutes. After cooling to room temperature, the reaction mixture was diluted with water and extracted with ethyl acetate. The organic layer was washed with saturated brine and then the solvent was evaporated. The resulting residue was purified by a silica gel column chromatography (toluene-ethyl acetate) and then recrystallized from ethyl acetate to obtain 590 mg of ethyl N-[4-(3-chlorophenyl)-1-ethyl-7-methyl-2-oxo-1,2-dihydro-1,8-naphthyridin-3-yl]carbamate as colorless crystals.

EXAMPLE 10

A 720 mg portion of ethyl N-[4-(3-chlorophenyl)-1-ethyl-7-methyl-2-oxo-1,2-dihydro-1,8-naphthyridin-3-yl] carbamate was stirred in 40 ml of an ethanol-3M sodium hydroxide aqueous solution (1:1) under heating at an oil bath temperature of 100° C. for 4 hours. After cooling to room temperature, the reaction mixture was diluted with water and then extracted with ethyl acetate. The organic layer was washed with saturated brine and the solvent was evaporated. The resulting residue was purified by a silica gel column chromatography (toluene-ethyl acetate) and then recrystallized from diisopropyl ether-ethyl acetate to obtain 298 mg of 3-amino-4-(3-chlorophenyl)-1-ethyl-7-methyl-1,8-naphthyridin-2(1H)-one as colorless crystals.

EXAMPLE 12

To a 15 ml dichloroethane solution containing 1.38 g of 3-(2-aminoethyl)-4-(3-chlorophenyl)-1-ethyl-7-methyl-1,8-naphthyridin-2(1H)-one were added 720 mg of a 37% formalin aqueous solution and 0.55 ml of acetic acid under cooling at 0° C., followed by stirring for 30 minutes. Then, 2.05 g of sodium triacetoxyborohydride was added thereto, and the whole was warmed to room temperature and then stirred for 2 hours. The reaction mixture was cooled to 0° C., adjusted to about pH 8 with a 1M sodium hydroxide aqueous solution, and extracted with chloroform. The solvent was evaporated from the organic layer and the residue was purified by a silica gel column chromatography (chloroform-methanol). To the resulting oily substance in 5 ml of methanol was added 194 mg of oxalic acid and then the solvent was evaporated. The resulting crude crystals were recrystallized from acetonitrile to obtain 300 mg of 4-(3-chlorophenyl)-3-(2-dimethylaminoethyl)-1-ethyl-7-methylnaphthyridin-2(1H)-one monooxalate 0.5 hydrate as colorless crystals.

EXAMPLE 13

To a 5 ml DMF solution containing 1.00 g of 3-amino-4-(3-chlorophenyl)-1-ethyl-7-methyl-1,8-naphthyridin-2 (1H)-one was added 191 mg of 60% sodium hydride, followed by warming to 60° C. To the reaction mixture were added 551 mg of N-(2-chloroethyl)dimethylamine hydrochloride and 1.08 ml of triethylamine together with 5 ml of DMF and the whole was stirred for 1 hour. After cooling to 0° C., the reaction mixture was diluted with 5 ml of water and extracted with ethyl acetate. The organic layer was washed with saturated brine and then the solvent was evaporated. The residue was purified by a silica gel column chromatography (chloroform-methanol). To the resulting oily substance in 5 ml of methanol was added 83 mg of oxalic acid and then the solvent was evaporated. The resulting crude crystals were recrystallized from methanol to obtain 93 mg of 4-(3-chlorophenyl)-3-(2-dimethylaminoethylamino)-1-ethyl-7-methyl-1,8-naphthyridin-2(1H)-one monooxalate 0.5 hydrate as colorless crystals.

EXAMPLE 14

To a 10 ml dichloroethane solution containing 630 mg of 3-(3-aminopropyl)-4-(3-chlorophenyl)-1-ethyl-7-methyl-1, 8-naphthyridin-2(1H)-one were added 243 mg of methanesulfonyl chloride and 0.30 ml of triethylamine under ice cooling, followed by stirring for 1 hour with warming to room temperature. The reaction mixture was diluted with ethyl acetate and washed with saturated sodium bicarbonate aqueous solution and saturated brine. The solvent was evaporated from the organic layer and the resulting residue was purified by a silica gel column chromatography (hexane-ethyl acetate) and then recrystallized from ethanol-water to obtain 204 mg of N-{3-[4-(3-chlorophenyl)-1-ethyl-7-methyl-2-oxo-1,2-dihydro-1,8-naphthyridin-3-yl] propyl}methanesulfonamide as colorless crystals.

EXAMPLE 16

A mixture of 1.00 g of 3-[4-(3-chlorophenyl)-1-ethyl-7-methyl-2-oxo-1,2-dihydro-1,8-naphthyridin-3-yl]propanoic acid, 20 ml of methanol and 0.5 ml of concentrated sulfuric acid was heated under reflux for a whole day and night. After cooling to room temperature, saturated sodium bicarbonate aqueous solution was added thereto and the whole was extracted with ethyl acetate. The organic layer was washed with water and saturated brine and then the solvent was evaporated. The residue was purified by a silica gel column chromatography (hexane-ethyl acetate). The resulting compound was dissolved in 20 ml of THF and 500 mg of sodium borohydride was added thereto. While heating under reflux, 3 ml of methanol was added dropwise thereto, and the mixture was further heated under reflux for 3 hours. After cooling to room temperature, 1M hydrochloric acid was added and the whole was extracted with ethyl acetate. The organic layer was washed with water and saturated brine and then the solvent was evaporated. The resulting residue was purified by a silica gel column chromatography (hexane-ethyl acetate) and then recrystallized from diisopropyl ether to obtain 497 mg of 4-(3-chlorophenyl)-1-ethyl-3-(3-hydroxypropyl)-7-methyl-1,8-naphthyridin-2(1H)-one as colorless crystals.

EXAMPLE 17

Under ice cooling, 5.60 ml of triethylamine and 4.90 ml of pivaloyl chloride were added to an 80 ml THF solution containing 5.08 g of 5-ketohexanoic acid, followed by stirring at room temperature for 1 hour. The reaction mixture was filtrated and the solvent was evaporated. To the resulting residue obtained by evaporating the solvent was added 2.00 g of 3-(3-chlorobenzoyl)-2-ethylamino-6-methylpyridine and the whole was stirred under heating at 150° C. for 2 days. After cooling to room temperature, the reaction mixture was diluted with ethyl acetate and washed with a 1M sodium hydroxide aqueous solution and saturated brine. The solvent of the organic layer was evaporated and the resulting residue was purified by a silica gel column chromatography (hexane-ethyl acetate) and then recrystallized from ethanol to obtain 774 mg of 4-(3-chlorophenyl)-1-ethyl-7-methyl-3-(3-oxobutyl)-1,8-naphthyridin-2(1H)-one as yellow crystals.

EXAMPLE 18

A mixture of 700 mg of 4-(3-chlorophenyl)-3-(2-cyanoethyl)-1-ethyl-7-methyl-1,8-naphthyridin-2(1H)-one, 388 mg of sodium azide, 411 mg of triethylamine hydrochloride and 10 ml of 1-methylpyrrolidin-2-one were stirred at 130° C. for 20 hours. The reaction mixture was cooled to room temperature, acidified by adding 1M hydrochloric acid and then extracted with ethyl acetate. The organic layer was washed with water and saturated brine and the solvent was evaporated. The residue was purified by a silica gel column chromatography (hexane-ethyl acetate) and then recrystallized from ethyl acetate-diisopropyl ether to obtain 130 mg of 4-(3-chlorophenyl)-1-ethyl-7-methyl-3-[2-(1H-tetrazol-5-yl)ethyl]-1,8-naphthyridin-2(1H)-one as pale yellow crystals.

EXAMPLE 19

To a 10 ml THF solution containing 500 mg of 4-(3-chlorophenyl)-1-ethyl-3-(3-hydroxypropyl)-7-methyl-1,8-naphthyridin-2(1H)-one were added 300 mg of p-toluenesulfonyl chloride, 0.15 ml of triethylamine and a catalytic amount of 4-dimethylaminopyridine, followed by heating under reflux for 2 hours. Then, 300 mg of p-toluenesulfonyl chloride, 0.15 ml of triethylamine and a catalytic amount of 4-dimethylaminopyridine were further added thereto, followed by heating under reflux for 2 hours. After cooling to room temperature, water was added and the mixture was extracted with ethyl acetate. The organic layer was washed with water and saturated brine and then the solvent was evaporated under a reduced pressure. The residue was purified by a silica gel column chromatography (hexane-ethyl acetate) and the resulting compound was stirred with 300 mg of imidazole, 250 mg of potassium carbonate and 10 ml of DMF under heating on an oil bath of 80° C. for 2 hours. Then, 300 mg of potassium iodide was added thereto, followed by stirring under heating on an oil bath of 80° C. for another 2 hours. After cooling to room temperature, the reaction mixture was diluted with water and then extracted with ethyl acetate. The organic layer was washed with water and saturated brine and then the solvent was evaporated. The resulting residue was purified by a silica gel column chromatography (chloroform-methanol-aqueous ammonia) and then dissolved in ethyl acetate. A 4M ethyl acetate solution of hydrogen chloride was added thereto and then the solvent was evaporated under a reduced pressure. The residue was recrystallized from acetonitrile-ethyl acetate to obtain 447 mg of 4-(3-chlorophenyl)-1-ethyl-3-[3-(imidazol-1-yl)propyl]-7-methyl-1,8-naphthyridin-2(1H)-one monohydrochloride 0.2 hydrate as colorless crystalline solid.

EXAMPLE 20

A 1.40 g portion of methyl 2-[4-(3-chlorophenyl)-1-ethyl-7-methyl-2-oxo-1,2-dihydro-1,8-naphthyridin-3-yl]benzoate was stirred in 20 ml of methanol and 10 ml of a 1M sodium hydroxide aqueous solution at 60° C. for 15 hours. The reaction mixture was cooled to room temperature and 10 ml of 1M hydrochloric acid was added thereto. The resulting precipitates were collected by filtration and recrystallized from ethyl acetate-diisopropyl ether to obtain 540 mg of 2-[4-(3-chlorophenyl)-1-ethyl-7-methyl-2-oxo-1,2-dihydro-1,8-naphthyridin-3-yl]benzoic acid 0.6 hydrate as a colorless crystalline solid.

EXAMPLE 21

A mixture of 700 mg of 4-(3-chlorophenyl)-1-ethyl-7-methyl-3-(3-trifluoromethylphenyl)-1,8-naphthyridin-2(1H)-one and 5 ml of concentrated sulfuric acid was stirred at 120° C. for 2 hours. The reaction mixture was poured into ice-water and extracted with ethyl acetate. The organic layer was washed with water and saturated brine and then the solvent was evaporated. The resulting crude crystals were recrystallized from acetonitrile to obtain 459 mg of 3-[4-(3-chlorophenyl)-1-ethyl-7-methyl-2-oxo-1,2-dihydro-1,8-naphthyridin-3-yl]benzoic acid as pale yellow crystals.

EXAMPLE 22

Under ice-cooling, 897 mg of sodium methoxide was added to a 40 ml methanol solution containing 3.45 g of 3-(4-methoxycarbonylphenyl)propanoic acid, followed by stirring for 30 minutes. After concentration of the reaction mixture, the resulting residue was diluted with 50 ml of THF. Under ice-cooling, 3.07 ml of pivaloyl chloride was added thereto, followed by stirring at room temperature for 1 hour. To the residue obtained by concentration of the reaction mixture after filtration was added 800 mg of 3-(3-chlorobenzoyl)-2-ethylamino-6-methylpyridine, followed by stirring at 150° C. for 14 hours. After cooling to room temperature, the reaction mixture was diluted with ethyl acetate and washed with a 1M sodium hydroxide aqueous solution and saturated brine. The solvent was evaporated from the organic layer and 50 ml of methanol and 900 mg of sodium methoxide were added to the residue, followed by heating under reflux for 3 hours. Thereafter, 40 ml of a 1M sodium hydroxide aqueous solution was added and the mixture was stirred at 60° C. for 16 hours. Then, 50 ml of 1M hydrochloric acid was added to the reaction mixture. After concentration under a reduced pressure, the resulting residue was diluted with ethyl acetate and washed with saturate sodium bicarbonate aqueous solution and saturated brine. After evaporation of the solvent, the resulting crude crystals were recrystallized from ethanol to obtain 764 mg of 4-{[4-(3-chlorophenyl)-1-ethyl-7-methyl-2-oxo-1,2-dihydro-1,8-naphthyridin-3-yl]methyl)benzoic acid as pale yellow crystals.

EXAMPLE 23

To a 20 ml dioxane solution containing 783 mg of 3-[4-(3-chlorophenyl)-1-ethyl-7-methyl-2-oxo-1,2-dihydro-1,8-naphthyridin-3-yl]benzoic acid were added 0.48 ml of DPPA, 0.31 ml of triethylamine and 0.89 ml of t-butanol, followed by heating under reflux for 18 hours. After cooling to room temperature and concentration of the reaction mixture under a reduced pressure, ethyl acetate was added to the resulting residue, followed by washing with saturate sodium bicarbonate aqueous solution and saturated brine. The organic layer was concentrated under a reduced pressure and the resulting residue was purified by a silica gel column chromatography (hexane-ethyl acetate). To 680 mg portion of 680 mg of thus obtained compound in 5 ml of ethyl acetate was added 5 ml of a 4M hydrogen chloride-ethyl acetate solution under ice cooling, followed by stirring at room temperature for 2 hours. The reaction mixture was concentrated and the resulting crude crystals were recrystallized from ethanol-ethyl acetate to obtain 486 mg of 3-(3-aminophenyl)-4-(3-chlorophenyl)-1-ethyl-7-methyl-1,8-naphthyridin-2(1H)-one monohydrochloride as pale brown crystals.

EXAMPLE 26

To a 50 ml methanol solution containing 3.16 g of 4-pyridylacetic acid monohydrochloride was added 1.97 g of sodium methoxide under ice cooling, and the whole was continued to stir for 1 hour. The reaction mixture was concentrated and 50 ml of THF was added to the residue. Under ice cooling, 2.24 ml of pivaloyl chloride was added thereto. Thereafter, the resulting mixture was treated in a similar manner to Example 17 and then subjected to a salt forming treatment to obtain 98 mg of 4-(3-chlorophenyl)-1-ethyl-7-methyl-3-(pyridin-4-yl)-1,8-naphthyridin-2(1H)-one monohydrochloride as pale yellow crystals.

EXAMPLE 28

A mixed solution containing 400 mg of 3-(1-acetylpiperidin-4-yl)-4-(3-chlorophenyl)-1-ethyl-7-methyl-1,8-naphthyridin-2(1H)-one, 5 ml of ethanol and 5 ml of 6M hydrochloric acid was heated under reflux for 15 hours. The reaction mixture was concentrated and, after addition of a saturated sodium bicarbonate aqueous solution, extracted with chloroform. The organic layer was washed with water and saturated brine, and then the solvent was evaporated. The residue was purified by a silica gel column chromatography (chloroform-methanol-aqueous ammonia), and the resulting yellow oily substance was dissolved in 5 ml of methanol to which was subsequently added a 1 ml methanol solution containing 45 mg of fumaric acid. The solvent was evaporated and the resulting residue was recrystallized from ethanol-ethyl acetate to obtain 187 mg of 4-(3-chlorophenyl)-1-ethyl-7-methyl-3-(piperidin-4-yl)-1,8-naphthyridin-2(1H)-one monofumarate as pale yellow crystals.

EXAMPLE 29

To a 20 ml chloroform solution containing 510 mg of 4-(3-chlorophenyl)-1-ethyl-3-(3-oxobutyl)-7-methyl-1,8-naphthyridin-2(1H)-one was added dropwise 1.03 ml of bromine under ice cooling. After the addition, saturated sodium thiosulfate aqueous solution was added to the reaction mixture, the whole was extracted with chloroform, and the organic layer was washed with saturated brine. The organic layer was dried over anhydrous magnesium sulfate and then, the solvent was evaporated. The resulting compound was dissolved in 10 ml of ethanol, 104 mg of thioacetamide was added thereto, and the whole was stirred at 70° C. for 2 hours. The solvent of the reaction mixture was evaporated and chloroform was added to the resulting residue. The solution was washed with water and saturated brine and dried over anhydrous magnesium sulfate. The solvent of the organic layer was evaporated and the residue was purified by a silica gel column chromatography (ethyl acetate-hexane) and then recrystallized from acetonitrile to obtain 301 mg of 4-(3-chlorophenyl)-3-[(2,4-dimethylthiazol-5-yl)methyl]-1-ethyl-7-methyl-1,8-naphthyridin-2(1H)-one as colorless crystals.

EXAMPLE 30

To 670 mg of 4-(3-chlorophenyl)-1-ethyl-7-methyl-3-(1-oxypyridine-4-yl)-1,8-naphthyridin-2(1H)-one were added 1.6 ml of phosphorus oxychloride and 2.4 ml of triethylamine, followed by stirring at 60° C. for 1 hour. The solvent was evaporated and water was added to the resulting residue. The mixture was extracted with ethyl acetate, and the organic layer was washed with saturated brine and dried over anhydrous magnesium sulfate. The solvent was evaporated and the resulting residue was purified by a silica gel column chromatography (ethyl acetate-hexane) and then recrystallized from ethanol-water to obtain 175 mg of 4-(3-chlorophenyl)-3-(2-chloropyridin-4-yl)-1-ethyl-7-methyl-1,8-naphthyridin-2(1H)-one as colorless crystals.

EXAMPLE 32

To a 10 ml ethyl acetate solution containing 570 mg of 3-(1-tert-butoxycarbonylpiperazin-4-yl)-4-(3-chlorophenyl)-1-ethyl-7-methyl-1,8-naphthyridin-2(1H)-one was added a 10 ml 4M hydrogen chloride-ethyl acetate solution, followed by stirring at room temperature for 1 hour. After adding water, the reaction mixture was neutralized with 1M sodium hydroxide aqueous solution, and then extracted with ethyl acetate. The organic layer was washed with saturated brine and dried over anhydrous magnesium sulfate. The solvent was evaporated and the residue was purified by a silica gel column chromatography (chloroform-methanol-aqueous ammonia) and then recrystallized from diisopropyl ether to obtain 115 mg of 4-(3-chlorophenyl)-1-ethyl-7-methyl-3-(piperazin-1-yl)-1,8-naphthyridin-2(1H)-one as pale yellow crystals.

EXAMPLE 34

To a 10 ml DMF solution containing 500 mg of 4-(3-chlorophenyl)-1-ethyl-3-(3-hydroxypropyl)-7-methyl-1,8-naphthyridin-2(1H)-one were added 500 mg of potassium carbonate and 0.5 ml of methyl iodide, followed by stirring under heating at an oil bath temperature of 80° C. for 2 hours. Thereafter, 1.0 g of potassium carbonate and 1.0 ml of methyl iodide were further added thereto, followed by stirring under heating at an oil bath temperature of 80° C. for a whole day and night. After the reaction mixture was cooled to room temperature, water was added thereto, and the whole was extracted with ethyl acetate. The organic layer was washed with water and saturated brine and dried over anhydrous magnesium sulfate. The solvent was evaporated and the residue was purified by a silica gel column chromatography (hexane-ethyl acetate) and then recrystallized from hexane-diisopropyl ether to obtain 160 mg of 4-(3-chlorophenyl)-1-ethyl-3-[3-(methoxycarbonyloxy)propyl]-7-methyl-1,8-naphthyridin-2(1H)-one as colorless crystals.

EXAMPLE 35

To a 10 ml tert-butanol solution containing 500 mg of 4-(3-chlorophenyl)-1-ethyl-3-(3-hydroxypropyl)-7-methyl-1,8-naphthyridin-2(1H)-one were added 300 mg of sodium tert-butoxide and 0.2 ml of methyl iodide successively, followed by stirring under heating at an oil bath temperature of 60° C. for 2 hours. After the reaction mixture was cooled to room temperature, water and 1M hydrochloric acid were added thereto, and the whole was extracted with ethyl acetate. The organic layer was washed with saturated brine and dried over anhydrous magnesium sulfate. The solvent was evaporated and the residue was purified by a silica gel column chromatography (hexane-ethyl acetate) and then recrystallized from diisopropyl ether to obtain 180 mg of 4-(3-chlorophenyl)-1-ethyl-3-(3-methoxypropyl)-7-methyl-1,8-naphthyridin-2(1H)-one as colorless crystals.

EXAMPLE 36

To a 60 ml ethanol solution containing 3.54 g of ethyl (8-methyl-8-azabicyclo[3.2.1]octan-3-yl)acetate was added 30 ml of 1M sodium hydroxide aqueous solution, followed by stirring at room temperature for 14 hours. Thereafter, 30 ml of 1M hydrochloric acid was added to the reaction mixture and the solvent was evaporated. Ethanol was added to the resulting residue and, after removal of insoluble matter by filtration, the solvent was again evaporated to obtain 3.55 g of a crude product. A 3.50 g portion of the compound was dissolved in 40 ml of methanol and 837 mg of sodium methoxide to form a sodium salt. After evaporation of methanol, the resulting residue was suspended in 40 ml of THF and 2.87 ml of pivaloyl chloride, followed by stirring at room temperature for 2 hours. Diethyl ether was added to the reaction mixture and, after removal of insoluble matter by filtration, the solvent was evaporated. To the resulting residue was added 800 mg of 3-(3-bromobenzoyl)-2-ethylamino-6-methylpyridine, followed by stirring at 150° C. for 14 hours. Ethyl acetate was added to the reaction mixture and the solution was washed with 1M sodium hydroxide aqueous solution, water and saturated brine, and then dried over anhydrous magnesium sulfate. After evaporation of the solvent, 50 ml of ethanol and 837 mg of sodium methoxide were added to the resulting residue, followed by heating under reflux for 1 hour. After evaporation of the solvent, ethyl acetate was added and the solution was washed with water and saturated brine and then dried over anhydrous magnesium sulfate. The solvent was evaporated and the resulting residue was purified by a silica gel column chromatography (chloroform-methanol-29% aqueous ammonia) to obtain 150 mg of a product. The compound was treated with 4M hydrogen chloride to form the hydrochloride, which was then recrystallized from ethanol-ethyl acetate to obtain 69 mg of 4-(3-chlorophenyl)-1-ethyl-7-methyl-3-(8-methyl-8-azabicyclo[3.2.1]octan-3-yl)-1,8-naphthyridin-2(1H)-one monohydrochloride as colorless crystals.

EXAMPLE 37

To a 10 ml THF solution containing 700 mg of 4-(3-chlorophenyl)-1-ethyl-3-(3-methanesulfonyloxypropyl)-7-methyl-1,8-naphthyridin-2(1H)-one were added 0.5 ml of pyrrolidine and 300 mg of potassium iodide, followed by stirring under heating at an oil bath temperature of 60° C. for 1.5 hours. After cooling to room temperature, water and 1M hydrochloric acid were added thereto, and the whole was extracted with ethyl acetate. The organic layer was washed with saturated brine and dried over anhydrous magnesium sulfate. Then, the solvent was evaporated and the residue was purified by a silica gel column chromatography (chloroform-methanol-aqueous ammonia). The resulting compound was dissolved in ethyl acetate and a 4M hydrogen chloride-ethyl acetate solution was added thereto. Thereafter, the residue obtained by evaporation of the solvent was recrystallized from ethyl acetate-acetonitrile to obtain 133 mg of 4-(3-chlorophenyl)-1-ethyl-7-methyl-3-[3-(pyrrolidin-1-yl)propyl]-1,8-naphthyridin-2(1H)-one monohydrochloride as colorless crystals.

EXAMPLE 38

To a mixture of 2.00 g of 4-(3-chlorophenyl)-1-ethyl-3-(2-hydroxyethyl)-7-methyl-1,8-naphthyridin-2(1H)-one, 1.0 ml of triethylamine and 20 ml of THF was added dropwise 0.5 ml of methanesulfonyl chloride, followed by stirring at room temperature for 30 minutes. Water was added to the reaction mixture and the whole was extracted with ethyl acetate. The organic layer was washed with 1M hydrochloric acid, saturated sodium bicarbonate aqueous solution and saturated brine, successively and then dried over anhydrous magnesium sulfate. To a 20 ml THF solution of the residue obtained by evaporation of the solvent were added 1.0 ml of triethylamine, 1.0 ml of ethyl isonipecotate and 500 mg of potassium iodide, followed by stirring under heating at an oil bath temperature of 60° C. for a whole day and night. After the reaction mixture was cooled to room temperature, water was added thereto, and the whole was extracted with ethyl acetate. The organic layer was washed with saturated brine and dried over anhydrous magnesium sulfate. After evaporation of the solvent, the resulting residue was purified by a silica gel column chromatography (chloroform-methanol) to obtain 1.70 g of an ester compound. Thereafter, in a similar manner to Example 2, 593 mg of 1-{2-[4-(3-chlorophenyl)-1-ethyl-7-methyl-2-oxo-1,2-dihydro-1,8-naphthyridin-3-yl]ethyl}piperidine-4-carboxylic acid was obtained as colorless crystals.

EXAMPLE 39

To a 15 ml 1,4-dioxane solution containing 314 mg of 3-(2-aminoethyl)-4-(3-chlorophenyl)-1-ethyl-7-methyl-1,8-naphthyridin-2(1H)-one were added 404 mg of 1-amidinopyrazole monohydrochloride and 0.48 ml of diisopropylethylamine, followed by stirring for 122 hours. The reaction solution was evaporated, the resulting solid was removed by filtration, and the solid was further washed with chloroform. The combine filtrate and washings were concentrated and the residue was purified by a silica gel column chromatography (chloroform-methanol-aqueous ammonia). The resulting oily substance was dissolved in 5 ml of ethanol, and 0.5 ml of 4M hydrogen chloride-ethyl acetate and acetonitrile were added thereto successively. The solvent was evaporated to obtain 347 mg of 4-(3-chlorophenyl)-1-ethyl-3-(2-guanidinoethyl)-7-methyl-1,8-naphthyridin-2(1H)-one monohydrochloride monohydrate as a colorless solid.

EXAMPLE 40

Hydrogen chloride gas was bubbled into 20 ml of an ethanol-chloroform (1:1) solution containing 461 mg of 4-(3-chlorophenyl)-3-(2-cyanoethyl)-1-ethyl-7-methyl-1,8-naphthyridin-2(1H)-one at −78° C. for 30 minutes, the solution was stirred at 5° C. for 18 hours and then the reaction solution was evaporated. To the resulting solid were added 15 ml of ethanol and 505 mg of ammonium acetate, followed by stirring for 90 hours. The reaction solution was evaporated and the residue was purified by a silica gel column chromatography (chloroform-methanol-aqueous ammonia). A 0.4 ml portion of 4 M hydrogen chloride-ethyl acetate was added to the resulting oily substance in 5 ml of ethanol. After evaporation of the solvent, the resulting residue was recrystallized from ethanol-ethyl acetate to obtain 268 mg of 3-(2-amidinoethyl)-4-(3-chlorophenyl)-1-ethyl-7-methyl-1,8-naphthyridin-2(1H)-one monohydrochloride as colorless crystals.

EXAMPLE 42

To a 7 ml THF-ethanol (5:2) solution containing 300 mg of methyl 3-[4-(3-chlorophenyl)-1-ethyl-7-formyl-2-oxo-1,2-dihydro-1,8-naphthyridin-3-yl]propanoate was added 9 mg of sodium borohydride under ice cooling. After stirring for 1 hour, water was added to the reaction mixture and the whole was extracted with ethyl acetate. The organic layer was washed with saturated brine and then the solvent was evaporated. The residue was purified by a silica gel column chromatography (hexane-ethyl acetate). Using a 200 mg portion of 210 mg of the resulting compound, the compound was treated in a similar manner to Example 2 to obtain 130 mg of 3-[4-(3-chlorophenyl)-1-ethyl-7-hydroxymethyl-2-oxo-1,2-dihydro-1,8-naphthyridin-3-yl]propanoic acid as pale yellow crystals.

EXAMPLE 43

To a 33 ml methanol-pyridine (10:1) solution containing 1.50 g of methyl 3-[4-(3-chlorophenyl)-1-ethyl-7-formyl-2-oxo-1,2-dihydro-1,8-naphthyridin-3-yl]propanoate was added 300 mg of hydroxylamine hydrochloride under ice cooling. After stirring for 1 hour, the reaction mixture was diluted with water and extracted with ethyl acetate. The organic layer was washed with water and saturated brine and then the solvent was evaporated. The resulting residue was treated in a similar manner to Example 2 to obtain 72 mg of 3-[4-(3-chlorophenyl)-1-ethyl-7-hydroxyiminomethyl-2-oxo-1,2-dihydro-1,8-naphthyridin-3-yl]propanoic acid as colorless crystals.

EXAMPLE 44

In a sealed tube, a mixture of 4.4 g of 6-chloro-3-(3-chlorobenzoyl)-2-ethylaminopyridine, 5 ml of THF and 10 ml of a 40% methylamine aqueous solution was stirred under heating at an oil bath temperature of 100° C. for 2 hours. After cooling to room temperature, chloroform was added thereto. The organic layer was washed with water and saturated brine and then the solvent was evaporated. To the residue were added 2 ml of benzoyl chloride, 2 g of 4-dimethylaminopyridine and 100 ml of dichloroethane, followed by stirring under heating at an oil bath temperature of 80° C. for 2 hours. Then, 1 ml of benzoyl chloride and 1 g of 4-dimethylaminopyridine were further added and the whole was stirred under heating at an oil bath temperature of 100° C. for additional 1 hour. After cooling to room temperature, water was added to the mixture and the whole was extracted with chloroform. The organic layer was washed with water and saturated brine and then the solvent was evaporated. The residue was purified by a silica gel column chromatography (hexane-ethyl acetate). To a 50 ml DMF solution of the resulting compound was added 700 mg of 60% sodium hydride under ice cooling, followed by stirring for 30 minutes. Then, 2.7 ml of monoethyl chloroglutarate was added thereto, followed by stirring under heating at an oil bath temperature of 80° C. for 1 hour. Further, 2.7 ml of monoethyl chloroglutarate was added thereto, followed by stirring under heating at an oil bath temperature of 80° C. for another 1 hour. After cooling to room temperature, the mixture was diluted with water and extracted with ethyl acetate. The organic layer was washed with water and saturated brine and then the solvent was evaporated. The residue was purified by a silica gel column chromatography (hexane-ethyl acetate). The resulting compound was heated under reflux together with 1.5 g of sodium methoxide and 50 ml of ethanol for 1 hour. After cooling to room temperature, 2 ml of concentrated sulfuric acid was added to the reaction mixture and the whole was heated under reflux for a whole day and night. The reaction mixture was cooled to room temperature and, after addition of saturated sodium bicarbonate aqueous solution, extracted with ethyl acetate. The organic layer was washed with saturated brine and then the solvent was evaporated. The residue was purified by a silica gel column chromatography (hexane-ethyl acetate). Thus obtained compound was stirred in 10 ml of THF-methanol (1:1) and 20 ml of a 1M sodium hydroxide aqueous solution under heating at an oil bath temperature of 80° C. for 1 hour. After cooling to room temperature, the reaction mixture was adjusted to about pH 2 with 1M hydrochloric acid and then extracted with ethyl acetate. The organic layer was washed with saturated brine and then the solvent was evaporated. The resulting residue was recrystallized from acetonitrile to obtain 1.43 g of 3-[4-(3-chlorophenyl)-1-ethyl-7-methylamino-2-oxo-1,2-dihydro-1,8-naphthyridin-3-yl]propanoic acid as pale yellow crystals.

EXAMPLE 46

A mixture of 1.2 g of 3-(3-bromobenzoyl)-2-ethylamino-6-methylpyridine and 2.1 g of glutaric anhydride was stirred under heating at 150° C. for 15 hours. After cooling to room temperature, 10 ml of 1M hydrochloric acid was added thereto and the whole was heated under reflux for 1 hour. After cooling to room temperature, the reaction mixture was diluted with water and extracted with ethyl acetate. The organic layer was washed with saturated brine and then the solvent was evaporated. To the residue was added 50 ml of ethanol and 0.5 ml of concentrated sulfuric acid, followed by heating under reflux for 1 hour. The reaction mixture was cooled to room temperature, diluted with water and then extracted with ethyl acetate. The organic layer was washed with saturated brine and then the solvent was evaporated. The residue was purified by a silica gel column chromatography (chloroform). Thereafter, similar operations to those in Example 2 were carried out to obtain 1.00 g of 3-[4-(3-bromophenyl)-1-ethyl-7-methyl-2-oxo-1,2-dihydro-1,8-naphthyridin-3-yl]propanoic acid as pale yellow crystals.

EXAMPLE 47

To a 20 ml THF solution containing 2.34 g of 3-cyclohexanecarbonyl-2-ethylamino-6-methylpyridine were added 3 ml of monoethyl chloroglutarate and 2.8 ml of 2,6-lutidine, followed by stirring under heating at an oil bath temperature of 60° C. for 1 hour. After the reaction mixture was cooled to room temperature, water was added thereto, and the whole was extracted with ethyl acetate. The organic layer was washed with 3M hydrochloric acid, saturated sodium bicarbonate aqueous solution and saturated brine, and dried over anhydrous magnesium sulfate. The solvent was evaporated and 1.00 g of sodium methoxide was added to a 20 ml ethanol solution of the resulting residue, followed by heating under reflux for 1 hour. Then, 20 ml of a 1M sodium hydroxide aqueous solution was added to the reaction solution, followed by heating under reflex for another 1 hour. After the mixture was cooled to room temperature, water was added thereto, and the mixture was neutralized with 1M hydrochloric acid and then extracted with ethyl acetate. The organic layer was washed with saturated brine and dried over anhydrous magnesium sulfate. The solvent was evaporated and the residue was recrystallized from ethanol-water to obtain 764 mg of 3-(4-cyclohexyl-1-ethyl-7-methyl-2-oxo-1,2-dihydro-1,8-naphthyridin-3-yl) propanoic acid as colorless crystals.

EXAMPLE 52

To 370 mg of ethyl {4-[4-(3-bromophenyl)-1-ethyl-7-methyl-2-oxo-1,2-dihydro-1,8-naphthyridin-3-yl]piperidin-1-yl}acetate was added 5 ml of 6M hydrochloric acid, followed by stirring at 100° C. for 15 hours. After removal of the solvent, the resulting crude crystals were recrystallized from ethanol-acetonitrile to obtain 185 mg of {4-[4-(3-bromophenyl)-1-ethyl-7-methyl-2-oxo-1,2-dihydro-1,8-naphthyridin-3-yl]piperidin-1-yl}acetic acid monohydrochloride as colorless crystals.

EXAMPLE 55

To 1.28 g of 4-(3-bromophenyl)-3-(1-ethoxycarbonylpiperidin-4-yl)-1-ethyl-7-methyl-1,8-naphthyridin-2(1H)-one was added 20 ml of concentrated hydrochloric acid, followed by stirring at 100° C. for 3 hours. The solvent was evaporated and, after the residue was made alkaline by adding concentrated aqueous ammonia, the mixture was extracted with ethyl acetate. The organic layer was washed with saturated brine, and then dried over anhydrous sodium sulfate. After removal of the solvent from the organic layer, the resulting crude crystals were recrystallized from acetonitrile and then recrystallized from ethanol-water to obtain 357 mg of 4-(3-bromophenyl)-1-ethyl-7-methyl-3-(piperidin-4-yl)-1,8-naphthyridin-2(1H)-one as colorless crystals.

EXAMPLE 56

To a 30 ml methanol solution containing 2.56 g of imidazo[1,2-a]pyridin-3-ylacetic acid was added 783 mg of sodium methoxide, followed by stirring at room temperature for 30 minutes. The solvent was evaporated and 15 ml of N-methylpyrrolidone and 2.15 ml of pivaloyl chloride were added to the resulting residue, followed by stirring at room temperature for 2 hours. Then, 900 mg of 3-(3-bromobenzoyl)-2-ethylamino-6-methylpyridine was added thereto, and the whole was stirred at 150° C. for 16 hours. Water was added to the reaction solution and the mixture was extracted with ethyl acetate. The organic layer was washed with water and saturated brine and dried over anhydrous magnesium sulfate. After removal of the solvent, the residue was purified by a silica gel column chromatography (chloroform-methanol) and then recrystallized from acetonitrile to obtain 240 mg of 4-(3-bromophenyl)-1-ethyl-3-(imidazo[1,2-a]pyridin-3-yl)-7-methyl-1,8-naphthyridin-2(1H)-one as yellow crystals.

EXAMPLE 57

To a 5 ml acetonitrile solution containing 400 mg of 4-(3-bromophenyl)-1-ethyl-7-methyl-3-(piperidin-4-yl)-1,8-naphthyridin-2(1H)-one were added 0.11 ml of ethyl bromoacetate and 0.13 ml of triethylamine, followed by stirring at room temperature for 13 hours. Ethyl acetate was added to the reaction solution and the solution was washed with saturated sodium bicarbonate aqueous solution and saturated brine and dried over anhydrous magnesium sulfate. After removal of the solvent from the organic layer, the resulting residue was purified by a silica gel column chromatography (hexane-ethyl acetate) and then recrystallized from ethyl acetate-diisopropyl ether to obtain 120 mg of ethyl {4-[4-(3-bromophenyl)-1-ethyl-7-methyl-2-oxo-1,2-dihydro-1,8-naphthyridin-3-yl]piperidin-1-yl}acetate as colorless crystals.

In a similar manner to the above Examples, the compounds of Examples 1 to 81 shown in the following Tables 1 to 3 were obtained, respectively. Structures and physicochemical data of the compounds of Examples 1 to 81 are shown in Tables 1 to 3.

Furthermore, structures of the other compounds of the invention are shown in Tables 4 and 5. These can easily be synthesized using the above production methods, the methods described in Examples and methods obvious for those skilled in the art, or modified methods thereof.

TABLE 1

| Ex | Syn | X—R⁶ | Dat | Sal |
|----|-----|------|-----|-----|
| 1 | — | —CO₂Et | MP: 119–121; NMR1: 6.97(1H, d, J=7.8Hz), 1.39(3H, t, J=6.8Hz), 1.06(3H, t, J=7.1Hz) | |
| 2 | — | —(CH₂)₂CO₂H | MP: 149–151; NMR1: 6.93(1H, d, J=8.3Hz), 2.69–2.81(2H, m), 2.53–2.60(2H, m) | |
| 3 | — | -CMe₂CH₂-CO₂H (Me Me on same C, CO₂H) | MP: 146–147; NMR2: 7.08(1H, d, J=8.3Hz), 4.50(2H, q, J=6.8Hz), 0.87(6H, s) | |
| 4 | — | —CONH₂ | MP: 249–252; MS: 342 | |
| 5 | — | —(CH₂)₃C(O)-morpholine | MP: 195–197; NMR2: 7.11(1H, d, J=8.3Hz), 4.53(2H, q, J=7.0Hz), 3.46–3.50(4H, m) | |
| 6 | — | —(CH₂)₂CON(Me)₂ | MP: 134–136; NMR1: 6.88(1H, d, J=8.3Hz), 3.01(3H, s), 2.74(2H, t, J=8.3Hz) | |
| 7 | 5, 2 | —CONH—CH₂CO₂H | MP: 133–135; MS: 400 | 0.5 H₂O |
| 8 | 57, 2 | —N(CH₂CO₂H)₂ | MP: 191–194; NMR1: 7.06(1H, d, J=8.3Hz), 4.74(2H, q, J=7.0Hz), 3.66(4H, s) | |
| 9 | — | —NHCO₂Et | MP: 183–184; NMR1: 6.97(1H, d, J=8.3Hz), 4.69(2H, q, J=7.0Hz), 3.95(2H, q, J=7.2Hz) | |
| 10 | — | —NH₂ | MP: 167–171; MS: 314 | |
| 11 | 9, 10 | —CH₂NH₂ | NMR2: 7.20(1H, d, J=8.3Hz), 4.58(2H, q, J=7.0Hz), 3.60–3.68(2H, m) | 1.1 HCl 0.5 H₂O |
| 12 | — | —(CH₂)₂N(Me)₂ | MP: 186–187; NMR2: 7.13(1H, d, J=8.3Hz), 4.54(2H, q, J=7.0Hz), 2.62(6H, s) | 1 oxa 0.5 H₂O |
| 13 | — | —NH(CH₂)₂N(Me)₂ | MP: 212–215; MS: 385 | 1 oxa 0.5 H₂O |
| 14 | — | —(CH₂)₃NHSO₂Me | MP: 140–141; NMR2: 7.09(1H, d, J=7.8Hz), 4.53(2H, q, J=6.8Hz), 2.81(3H, s) | |
| 15 | 14 | —(CH₂)₃NHAc | MP: 151–154; NMR1: 6.91(1H, d, J=8.3Hz), 4.69(2H, q, J=7.0Hz), 1.98(3H, s) | |
| 16 | — | —(CH₂)₃OH | MP: 109–110; NMR1: 6.92(1H, d, J=7.8Hz), 4.71(2H, q, J=7.0Hz), 3.42–3.56(2H, m) | |
| 17 | — | —(CH₂)₂COMe | MP: 133–135; NMR2: 7.10(1H, d, J=8.3Hz), 4.52(2H, q, J=6.8Hz), 2.01(3H, s) | |
| 18 | — | —(CH₂)₂-(1H-tetrazol-5-yl) (propyl tetrazole) | MP: 181–183; NMR2: 7.10(1H, d, J=8.0Hz), 2.58(3H, s), 2.98–3.14(2H, m) | |
| 19 | — | —(CH₂)₄-imidazol-1-yl | MP: 196–201; NMR2: 9.06(1H, s), 7.11(1H, d, J=8.8Hz), 4.53(2H, q, J=6.8Hz) | 1 HCl 0.2 H₂O |
| 20 | — | 2-methylbenzoic acid (o-tolyl-CO₂H) | MP: 152–155; MS: 419 | 0.6 H₂O |

TABLE 1-continued
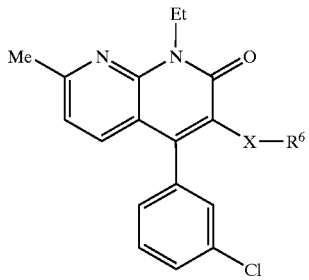
| Ex | Syn | X—R⁶ | Dat | Sal |
|---|---|---|---|---|
| 21 | — | 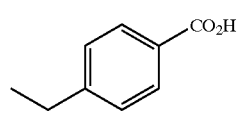 | MP: 254–256; MS: 419 | |
| 22 | — | 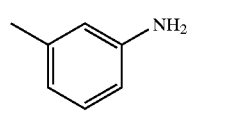 | MP: 235–237; MS: 433 | |
| 23 | — | 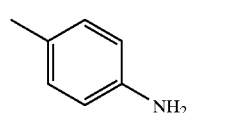 | MP: 207–212; MS: 390 | 1 HCl |
| 24 | 9, 10 | 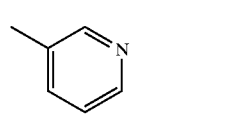 | MP: 177–185(dec); MS: 390 | 0.9 HCl 0.5 H₂O |
| 25 | 17 | 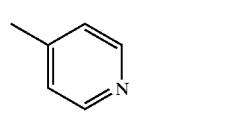 | MP: 211–213; NMR2: 8.28(1H, d, J=2.0Hz), 7.18(1H, d, J=7.8Hz), 4.56(2H, q, J=6.8Hz) | |
| 26 | — | 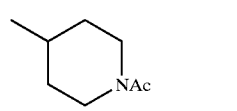 | MP: 190–195; NMR2: 8.80(2H, d, J=6.4Hz), 7.49(1H, d, J=8.3Hz), 4.57(2H, q, J=6.4Hz) | 1 HCl |
| 27 | 22 | 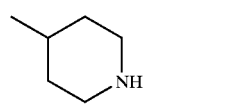 | MP: 221–223; NMR2: 7.08(1H, d, J=8.3Hz), 4.49(2H, q, J=6.9Hz), 1.97(3H, s) | |
| 28 | — | 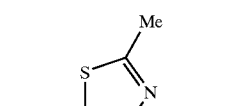 | MP: 225–227; NMR2: 7.08(1H, d, J=8.3Hz), 4.51(2H, q, J=6.8Hz), 1.50–1.62(2H, m) | 1 fum |
| 29 | — | 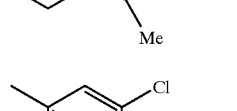 | MP: 156–158; MS: 424 | |
| 30 | — |  | MP: 176–177; MS: 410 | |

TABLE 1-continued

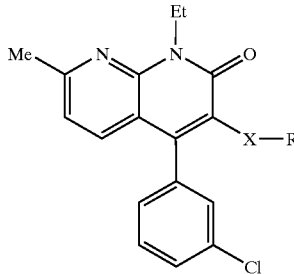

| Ex | Syn | X—R⁶ | Dat | Sal |
|---|---|---|---|---|
| 31 | 12 | 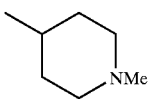 | MP: 250–253; MS: 396 | 1 fum |
| 32 | — |  | MP: 109–110; NMR1: 6.88(1H, d, J=7.8Hz), 4.66(2H, q, J=7.0Hz), 2.86–2.92(4H, m) | |
| 33 | 14 | —(CH₂)₃OAc | MP: 68–69; NMR1: 6.89(1H, d, J=8.3Hz), 4.67(2H, q, J=7.0Hz), 1.91(3H, s) | |
| 34 | — | —(CH₂)₃OCO₂Me | MP: 92–93; NMR1: 6.89(1H, d, J=7.8Hz), 4.67(2H, q, J=7.0Hz), 3.71(3H, s) | |
| 35 | — | —(CH₂)₃OMe | MP: 96–97; NMR1: 6.89(1H, d, J=7.8Hz), 4.67(2H, q, J=7.0Hz), 3.22(3H, s) | |
| 36 | — | 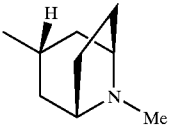 | NMR2: 7.59(1H, d, J=7.8Hz), 4.54(2H, q, J=6.8Hz), 2.95(1H, quint, J=9.8Hz); MS: 422 | 1 HCl |
| 37 | — | 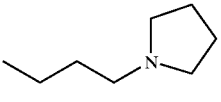 | MP: 208–213(dec.); NMR2: 7.12(1H, d, J=8.3Hz), 4.54(2H, q, J=7.0Hz), 2.94–3.02 (2H, m) | 1 HCl |
| 38 | — | 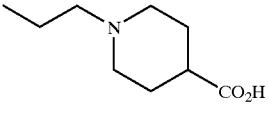 | MP: 142–146; NMR2: 7.08(1H, d, J=7.8Hz), 4.52(2H, q, J=6.8Hz), 2.04–2.14(1H, m) | |
| 39 | — | 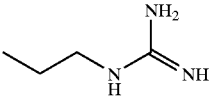 | MS: 384; NMR2: 9.57(1H, brs), 6.95–7.52 (3H, brs), 4.56(2H, q) | 1HCl 1 H₂O |
| 40 | — | 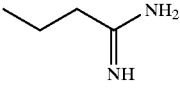 | MP: 228–230; NMR2: 8.83(2H, s), 8.60(2H, s), 4.54(2H, q) | 1 HCl |
| 58 | 1 | —CN | MP: 234–236; MS: 324 | |
| 59 | 2 | —CO₂H | MP: 206–210; NMR1: 15.0(1H, brs), 4.80 (2H, q, J=7.3Hz), 2.71(3H, s) | |
| 60 | 2 | —CH₂CO₂H | MP: 201–204; NMR2: 7.13(1H, d, J=8.3Hz), 4.52(2H, q, J=7.0Hz), 3.22(2H, s), | |
| 61 | 2 | —(CH₂)₃CO₂H | MP: 146–148; NMR2: 7.09(1H, d, J=8.3Hz), 4.52(2H, q, J=7.0Hz), 2.25–2.41(1H, m) | 0.3 H₂O |
| 62 | 2 | 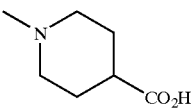 | MP: 243–245(dec); NMR2: 7.08(1H, d, J=8.3 Hz), 4.49(2H, q, J=6.92Hz), 2.07–2.18(1H, m) | |

TABLE 1-continued
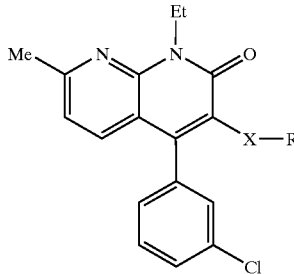
| Ex | Syn | X—R⁶ | Dat | Sal |
|---|---|---|---|---|
| 63 | 5 | 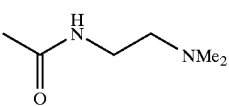 | MP: 187–191; NMR1: 6.96(2H, d, J=7.9Hz), 2.26–2.36(2H, m), 2.16(6H, s) | |
| 64 | 5 | 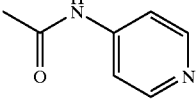 | MP: 258–260; NMR1: 11.8(1H, brs), 8.44 (2H, br), 7.39(1H, d, J=8.3Hz) | |
| 65 | 5 | 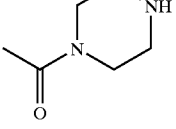 | MP: 236–238; MS: 411 | 0.6 H₂O |
| 66 | 5 | —(CH₂)₂CONH₂ | MP: 176–178 | |
| 67 | 10 | 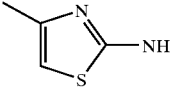 | MP: 232–234; NMR2: 7.13(1H, d, J=8.3Hz), 6.24(1H, s), 4.52(2H, q, J=6.8Hz) | |
| 68 | 11 | —(CH₂)₂NH₂ | MP: 171–175; NMR2: 7.09(1H, d, J=7.7Hz), 4.53(2H, q, J=6.8Hz), 2.80–2.93(2H, m) | 1 fum 1.5 EtOH |
| 69 | 11 | —(CH₂)₃NH₂ | MP: 213–216; NMR2: 7.11(1H, d, J=7.8Hz), 4.54(2H, q, J=7.0Hz), 2.29–2.43(2H, m) | 1 fum |
| 70 | 18 | 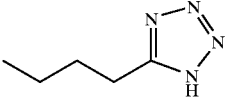 | MP: 155–158; NMR2: 15.86(1H, s), 7.10 (1H, d, J=8.1Hz), 4.52(2H, q, J=7.1Hz) | |
| 71 | 21 | 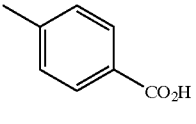 | MP: >300; NMR2: 7.76(2H, d, J=8.3Hz), 4.65(1H, q, J=8.3Hz), 4.55(2H, q, J=6.8Hz) | |
| 72 | 22 | 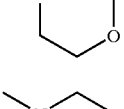 | MP: 155–156; NMR1: 6.89(1H, d, J=8.3Hz), 4.65(2H, q, J=6.8Hz), 3.53–3.56(2H, m) | |
| 73 | 22 | 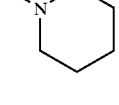 | MP: 141–143; NMR1: 6.86(1H, d, J=7.8Hz), 4.65(2H, q, J=6.9Hz), 2.83–2.89(2H, m) | |
| 74 | 37 | 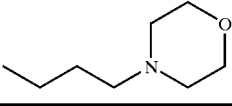 | MP: 217–225; NMR2: 7.12(1H, d, J=8.3Hz), 4.54(2H, q, J=7.0Hz), 3.86–3.94(2H, m) | 1 HCl |

TABLE 2

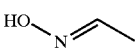

| Ex | Syn | R¹ | R² | R⁵ | Dat |
|---|---|---|---|---|---|
| 41 | 20 | Et | Cl | 3-Cl—Ph | MP: 197–199; NMR2: 7.29(1H, d, J=8.3Hz), 4.44(2H, q, J=6.8Hz), 2.30–2.42(2H, m) |
| 42 | — | Et | HO—CH₂ | 3-Cl—Ph | MP: 157–160; NMR2: 12.1(1H, s), 4.65(2H, d, J=5.9Hz), 4.52(2H, q, J=6.8Hz) |
| 43 | — | Et | HO-N=CH- | 3-Cl—Ph | MP: 234–238; NMR2: 8.16(1H, s), 4.54(2H, q, J=7.0Hz), 2.32–2.45(2H, m) |
| 44 | — | Et | Me—NH— | 3-Cl—Ph | MP: 202–204; NMR2: 6.86(1H, d, J=8.8Hz), 4.47(2H, q, J=6.83Hz), 2.89(3H, d, J=4.4Hz) |
| 45 | 2 | Et | MeS— | 3-Cl—Ph | MP: 167–168; NMR1: 6.96(1H, d, J=8.3Hz), 2.73(2H, q, J=7.4Hz), 2.66(3H, s) |
| 46 | — | Et | Me | 3-Br—Ph | MP: 161–162; NMR1: 7.39(1H, t, J=7.8Hz), 6.93(1H, d, J=8.3Hz), 2.66–2.81(2H, m) |
| 47 | — | Et | Me | cHex | MP: 155–156; NMR1: 4.64(2H, q, J=7.0Hz), 1.39–1.78(10H, m), 1.33 (3H, t, J=7.0Hz) |
| 75 | 41 | Et | Me | 2-Cl—Ph | MP: 181–183; MS: 371 |
| 76 | 46 | cPr—CH₂ | Me | 3-Cl—Ph | MP: 170–171; NMR1: 6.93(1H, d, J=8.3Hz), 4.54(1H, d, J=6.8Hz), 2.69–2.82(2H, m) |
| 77 | 46 | Et | Me | 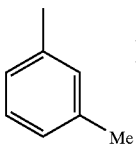 | MP: 174–175; NMR1: 4.70(2H, q, J=6.8Hz), 2.41(3H s), 1.39(3H, t, J=6.8Hz) |
| 78 | 46 | Et | Me | 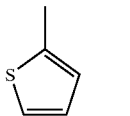 | MP: 188–189; NMR1: 7.19(1H, dd, J=4.9, 3.5Hz), 4.69(2H, q, J=6.8 Hz), 2.87(2H, t, J=7.3Hz) |

TABLE 3

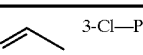

| Ex | Syn | R² | R⁵ | X—R⁶ | Dat | Sal |
|---|---|---|---|---|---|---|
| 48 | 6 | HO-N=CH- | 3-Cl—Ph | 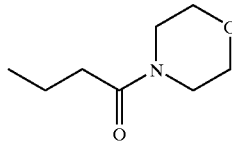 | MP: 188–190; NMR1: 11.97 (1H, s), 3.30–3.37(6H, m), 2.38–2.47(2H, m) | |

TABLE 3-continued

[Structure: 1,8-naphthyridin-2(1H)-one core with N1-Et, 3-(X—R⁶), 4-R⁵, 7-R²]

| Ex | Syn | R² | R⁵ | X—R⁶ | Dat | Sal |
|---|---|---|---|---|---|---|
| 49 | 42 | HO—CH₂ | 3-Cl—Ph | (propyl-C(O)-morpholine) | MP: 187–188; NMR1: 4.83 (2H, d, J=4.8Hz), 3.50–3.67 (8H, m), 2.74(2H, t, J=8.3Hz) | |
| 50 | 20 | HO—CH₂ | 3-Cl—Ph | (piperidin-4-yl CO₂H, N-methylene) | MS: 442; NMR2: 7.49(1H, d, J=8.3Hz), 4.81(2H, d, J=5.8 Hz), 2.13(1H, m) | |
| 51 | 17 | Me | 3-Br—Ph | (3-pyridyl methylene) | MP: 199–201; MS: 422 | 1 HCl |
| 52 | — | Me | 3-Br—Ph | (4-(CH₂CO₂H)-piperidine, N-methylene) | MP: >250(dec); NMR2: 7.35 (1H, d, J=7.3Hz), 4.02(2H, brs), 2.58(3H, s) | 1 HCl |
| 53 | 17 | Me | 3-Br—Ph | (2-Me-4-pyridyl methylene) | MP: 193–195; NMR1: 8.33 (1H, d, J=4.8Hz), 4.70(2H, q, J=7.0Hz), 2.66(3H, s) | |
| 54 | 17, 28 | Me | 3-Br—Ph | (4-ethyl-piperidine, NH) | MP: 225–230(dec); NMR2: 7.10 (1H, d, J=8.3Hz), 4.53(2H, q, J=6.8Hz), 1.00–1.16(1H, m) | 1 fum 0.5 H₂O |
| 55 | — | Me | 3-Br—Ph | (4-methyl-piperidine, NH) | MP: 195–197; MS: 426 | 0.5 fum 1 H₂O |
| 56 | — | Me | 3-Br—Ph | (3-methyl-imidazo[1,2-a]pyridine) | MP: 234–236; MS: 460 (M⁺) | |
| 57 | — | Me | 3-Br—Ph | (4-methyl-piperidine-N-CH₂CO₂Et) | MP: 176–177; MS: 512 | |
| 79 | 18 | Me | cHex | (propyl-tetrazole) | MP: 207–209; MS: 367 | |
| 80 | 18 | Me | 3-Br—Ph | (ethyl-tetrazole) | MP: 194–196; MS: 439 | |

TABLE 3-continued

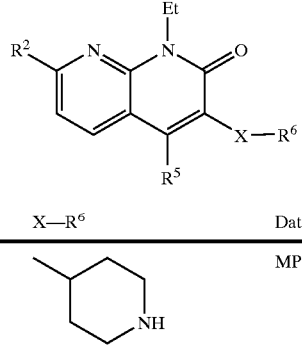

| Ex | Syn | R² | R⁵ | X—R⁶ | Dat | Sal |
|---|---|---|---|---|---|---|
| 81 | 28 | Me | cHex | 4-methylpiperidine | MP: 225–227; MS: 354 | 1 fum |

TABLE 4

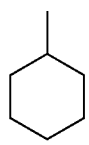

| No | R² | R⁵ | X—R⁶ |
|---|---|---|---|
| 1 | Me | cyclohexyl | (CH₂)₃CO₂H |
| 2 | | | (CH₂)₃-tetrazole |
| 3 | | | (CH₂)₂CO-morpholine |
| 4 | | | (CH₂)₂C(NH)NH₂ |
| 5 | | | (CH₂)₂NHC(NH)NH₂ |
| 6 | | | (CH₂)₂-N-piperidine-CO₂H |
| 7 | | | N-Me-piperidine-CO₂H |
| 8 | | Py4 | |
| 9 | | 3-bromophenyl | (CH₂)₃CO₂H |
| 10 | | | (CH₂)₃-tetrazole |
| 11 | | | (CH₂)₂CO-morpholine |
| 12 | | | (CH₂)₂C(NH)NH₂ |
| 13 | | | (CH₂)₂NHC(NH)NH₂ |
| 14 | | | (CH₂)₂-N-piperidine-CO₂H |
| 15 | | Py4 | |
| 16 | Cl | cyclohexyl | (CH₂)₂CO₂H |
| 17 | | | (CH₂)₂-tetrazole |
| 18 | | | (CH₂)₂C(NH)NH₂ |
| 19 | | 3-chlorophenyl | N-Me-piperidine-CO₂H |

TABLE 4-continued

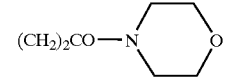

| No | R² | R⁵ | X—R⁶ |
|---|---|---|---|
| 20 | | | (CH₂)₂CO—morpholine |
| 21 | | Py4 | 3-bromophenyl |
| 22 | | | 4-methylpiperidine |
| 23 | HOCH₂ | cyclohexylmethyl | (CH₂)₂CO₂H |
| 24 | | | (CH₂)₂-tetrazole |
| 25 | | | (CH₂)₃-tetrazole |
| 26 | | | (CH₂)₃CO₂H |
| 27 | | | (CH₂)₂C(NH)NH₂ |
| 28 | | | (CH₂)₂CO—morpholine |
| 29 | | 3-bromophenyl | (CH₂)₂-N-piperidine-CO₂H |
| 30 | | | (CH₂)₂NHC(NH)NH₂ |
| 31 | | | N-methylpiperidine-CO₂H |
| 32 | | | 4-methylpiperidine |
| 33 | | Py4 | |

TABLE 4-continued

| No | R² | R⁵ | X—R⁶ |
|---|---|---|---|
| 34 | | 3-chlorophenyl | (CH₂)₃CO₂H |
| 35 | | | (CH₂)₂-tetrazole |
| 36 | | | (CH₂)₃-tetrazole |
| 37 | | | (CH₂)₂C(NH)NH₂ |
| 38 | | | (CH₂)₂NHC(NH)NH₂ |
| 39 | | | (CH₂)₂-N-piperidine-CO₂H |
| 40 | | Py4 | |
| 41 | | | 4-methylpiperidine |
| 42 | | | N-methylpiperidine-CO₂H |
| 43 | HON=CH | cyclohexylmethyl | (CH₂)₃CO₂H |
| 44 | | | N-methylpiperidine-CO₂H |

TABLE 5

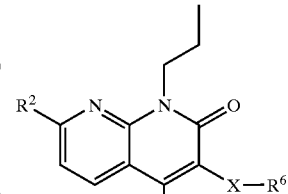

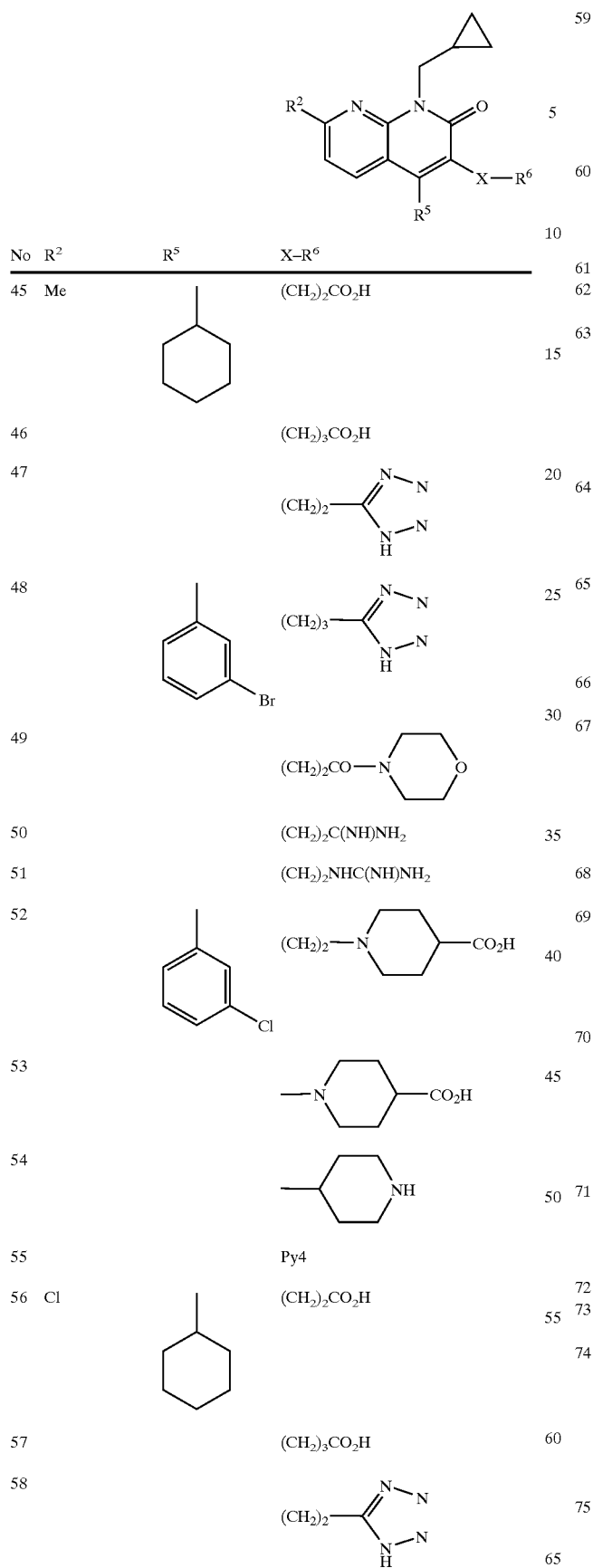
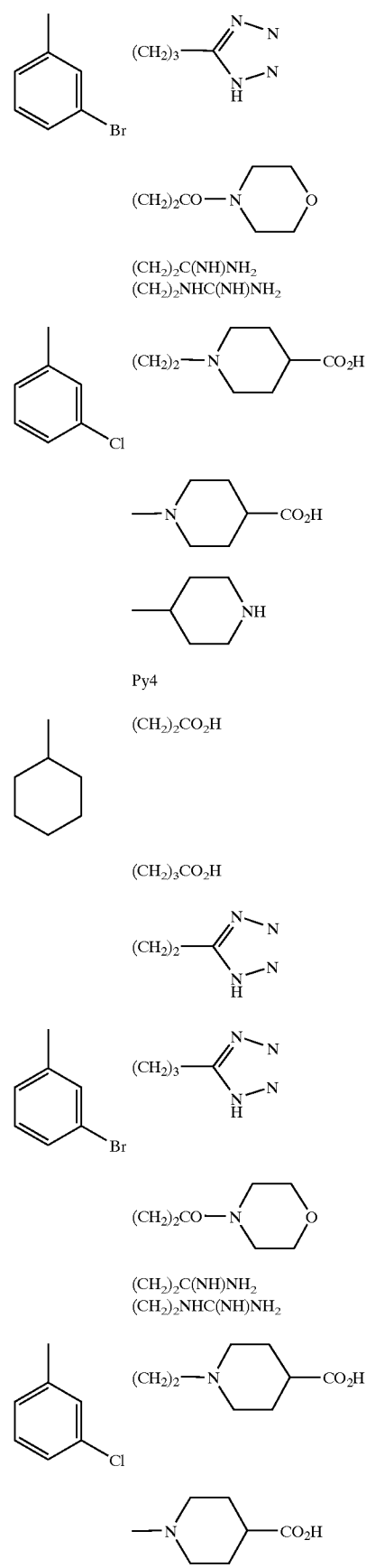

| 76 | 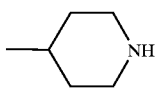 Py4 |
| 77 | |
| 78 | HON=CH (CH₂)₂CO₂H |
| | 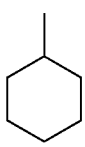 |
| 79 | (CH₂)₃CO₂H |
| 80 | 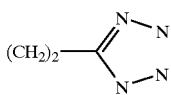 |
| 81 | 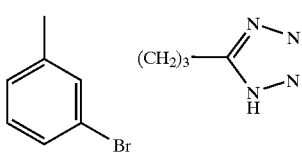 |
| 82 | 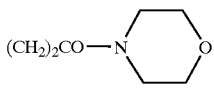 |
| 83 | (CH₂)₂C(NH)NH₂ |
| 84 | (CH₂)₂NHC(NH)NH₂ |
| 85 | 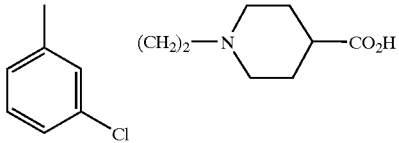 |
| 86 | 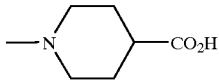 |
| 87 | 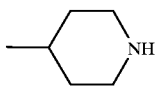 Py4 |
| 88 | |

What is claimed is:

1. A naphthynidine derivative represented by the following formula (I') or a pharmaceutically acceptable salt thereof

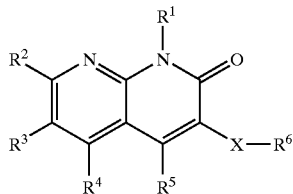

(I')

(wherein each symbol has the following meaning;
$R^1$: —$R^0$, -a lower alkylene-cycloalkyl or -a cycloalkyl
$R^0$: -a lower alkyl,
$R^2$, $R^3$, and $R^4$: —H, —$R^0$, -a halogen, -a lower alkylene-OH, -a lower alkylene-SH, -a lower-alkylene-O—$R^0$, -a lower alkylene-S—$R^0$, -a lower alkylene-O—CO—$R^0$, -a lower alkylene-S—CO—$R^0$, —OH, —O—$R^0$, —S—$R^0$, —SO—$R^0$, —SO₂—$R^0$, —NH₂, —NHR$^0$, —NR$^0$₂, -a cycloalkyl, —CO—$R^0$, or —CH=N—OR$^9$, which may be the same or different from one another, $R^9$: —H, —$R^0$ or -a lower alkylene-aryl, $R^5$: a cycloalkyl which may be substituted with a group selected from $R^{10}$, a cycloalkenyl which may be substituted with a group selected from $R^{10}$, or phenyl which may be substituted with a group selected from $R^{10}$, $R^6$: —OH, —OR$^7$, —COOH, —COOR$^7$, —CONH₂, —CONHR$^7$, —CON(R$^7$)₂, —O—COR$^7$, —O—COOR$^7$, —CHO, —COR$^7$, —NH₂, —NHR$^7$, —N(R$^7$)₂, —NHCOR$^7$, —N(R$^7$)COR$^7$, —NHSO₂R$^7$, —N(R$^7$)SO₂R$^7$, —CN, —NHCOOR$^7$, —N(R$^7$)COOR$^7$, —C(NH)NH₂, —NHC(NH)NH₂ or —N(R$^7$)C(NH)NH₂, or a group represented by the formula —Y—R$^8$, $R^7$: a lower alkyl which may be substituted with a group selected from the group consisting of —OH, -phenyl, -a halogen, —OR$^0$, —CO₂H, —CO₂R$^0$, —NH₂, —NHR$^0$, —NR$^0$₂, —NO₂, —CN, and —COR$^0$, $R^8$: a cycloalkyl which may be substituted with a group selected from $R^{10}$, an aryl which may be substituted with a group selected from $R^{10}$, or a heterocyclic group which may be substituted with a group selected from $R^{10}$, $R^{10}$: —OH, -phenyl, -a halogen, —OR$^0$, —CO₂H, —CO₂R$^0$, —NH₂, —NHR$^0$, —NRO₂, —NO₂, —CN or —COR$^0$, or a group described in $R^7$.

Y: a bond, —O—, —COO—, —CONH—, —CON(R$^7$)—, —O—CO—, —O—COO—, —CO—, —NH—, —N(R$^7$)—, —NHCO—, —N(R$^7$)CO—, —NHCOO—, —N(R$^7$)COO—, —NHSO₂—, or —N(R$^7$)SO₂—, and X: a bond, a lower alkylene, or a lower alkenylene, provided that, when X is a bond, then R$^6$ is —Y—R$^8$ and Y is a bond).

2. The naphthyridine derivative or a pharmaceutically acceptable salt thereof according to claim 1, wherein X is a bond or a lower alkylene and R$^6$ is —OH, —COOH, —COOR$^7$, —O—COR$^7$, —NH₂, —NHR$^7$, —N(R$^7$)₂, —C(NH)NH₂, —NHC(NH)NH₂ or —N(R$^7$)C(NH)NH₂, or a group represented by the formula —Y—R$^8$.

3. The naphthyridine derivative or a pharmaceutically acceptable salt thereof according to claim 1, wherein R$^5$ is cyclohexyl or phenyl substituted with a halogen.

4. The naphthyridine derivative or a pharmaceutically acceptable salt thereof according to claim 1, which is selected from the group consisting of 3-(2-amidinoethyl)-4-(3-chlorophenyl)-1-ethyl-7-methyl-1,8-naphthyridin-2(1H)-one, 4-(3-chlorophenyl)-1-ethyl-3-(2-guanidinoethyl)-7-methyl-1,8-naphthyridin-2(1H)-one, 4-cyclohexyl-1-ethyl-7-methyl-3-[2-(1H-tetrazol-5-yl)ethyl]-1,8-naphthyridin-2(1H)-one, 4-(3-chlorophenyl)-1-ethyl-7-methyl-3-[3-(1H-tetrazol-5-yl)propyl]-1,8-naphthyridin-2(1H)-one, 4-(3-bromophenyl)-1-ethyl-7-methyl-3-[2-(1H-tetrazol-5-yl)ethyl]-1,8-naphthyridin-2(1H)-one, 3-[4-(3-chlorophenyl)-1-ethyl-7-methyl-2-oxo-1,2-dihydro-1,8-naphthyridin-3-yl]propanoic acid, 3-(4-cyclohexyl-1-ethyl-7-methyl-2-oxo-1,2-dihydro-1,8-naphthyridin-3-yl)propanoic acid, 3-[4-(3-chlorophenyl)-1-ethyl-7-methyl-2-oxo-1,2-dihydro-1,8-naphthyridin-3-yl]benzoic acid, 3-[4-(3-chlorophenyl)-1-ethyl-7-(hydroxyiminomethyl)-2-oxo-1,2-dihydro-1,8-naphthyridin-3-yl]propanoic acid, 3-[7-chloro-4-(3-chlorophenyl)-1-ethyl-2-oxo-1,2-dihydro-1,8-naphthyridin- 3-yl]propanoic acid, 3-[1-ethyl-7-methyl-4-(3-methylphenyl)-2-oxo-1,2-dihydro-1,8-naphthyridin-3-yl]propanoic acid, 4-(3-chlorophenyl)-1-ethyl-7-methyl-3-(piperidin-4-yl)-1,8-naphthyridin-2(1H)-one and 1-{2-[4-(3-chlorophenyl)-1-ethyl-7-methyl-2-oxo-1,2-dihydro-1,8-naphthyridin-3-yl]ethyl}piperidine-4-carboxylic acid.

5. A pharmaceutical composition which comprises the naphthyridine derivative of claim 1 or a pharmaceutically acceptable salt thereof and a pharmaceutically acceptable carrier.

6. A pharmaceutical composition, which comprises a naphthyridine derivative represented by the following formula (I) or a pharmaceutically acceptable salt thereof as a type IV phosphodiesterase inhibitor, and a pharmaceutically acceptable carrier

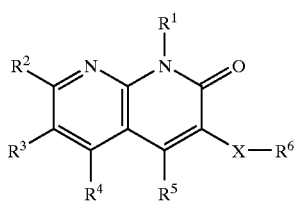

(I)

(wherein each symbol has the following meaning;

$R^1$: —$R^0$, -a lower alkylene-cycloalkyl or -a cycloalkyl $R^0$: -a lower alkyl, $R^2$, $R^3$, and $R^4$: —H, —$R^0$, -a halogen, -a lower alkylene-OH, -a lower alkylene-SH, -a lower alkylene-O—$R^0$, -a lower alkylene-S—$R^0$, -a lower alkylene-O—CO—$R^0$, -a lower alkylene-S—CO—$R^0$, —OH, —O—$R^0$, —S—$R^0$, —SO—$R^0$, —$SO_2$—$R^0$, —$NH_2$, —$NHR^0$, —$NR^0{}_2$, -a cycloalkyl, —CO—$R^0$, or —CH=N—$OR^9$, which may be the same or different from one another, $R^9$: —H, —$R^0$ or -a lower alkylene-aryl, $R^5$: a cycloalkyl which may be substituted with a group selected from $R^{10}$, a cycloalkenyl which may be substituted with a group selected from $R^{10}$, or phenyl which may be substituted with a group selected from $R^{10}$, $R^6$: —OH, —$OR^7$, —COOH, —$COOR^7$—$CONH_2$, —$CONHR^7$, —$CON(R^7)_2$, —O—$COR^7$, —O—$COOR^7$, —CHO, —$COR^7$, —$NH_2$, —$NHR^7$, —$N(R^7)_2$, —$NHCOR^7$, —$N(R^7)COR^7$, —$NHSO_2R^7$, —$N(R^7)SO_2R^7$, —CN, —$NHCOOR^7$, —$N(R^7)COOR^7$, —$C(NH)NH_2$, —$NHC(NH)NH_2$ or —$N(R^7)C(NH)NH_2$, or a group represented by the formula —Y—$R^8$, $R^7$: a lower alkyl which may be substituted with a group selected from the group consisting of —OH, -phenyl, -a halogen, —$OR^0$, —$CO_2H$, —$CO_2R^0$, —$NH_2$, —$NHR^0$, —$NR^0{}_2$, —$NO_2$, —CN, and —$COR^0$, $R^8$: a cycloalkyl which may be substituted with a group selected from $R^{10}$, an aryl which may be substituted with a group selected from $R^{10}$, or a heterocyclic group which may be substituted with a group selected from $R^{10}$, $R^{10}$: —OH, -phenyl, -a halogen, —$OR^0$, —$CO_2H$, —$CO_2R^0$, —$NH_2$, —$NHR^0$, —$NR^0{}_2$, —$NO_2$, —CN or —$COR^0$, or a group described in $R^7$.

Y: a bond, —O—, —COO—, —CONH—, —CON($R^7$)—, —O—CO—, —O—COO—, —CO—, —NH—, —N($R^7$)—, —NHCO—, —N($R^7$)CO—, —NHCOO—, —N($R^7$)COO—, —$NHSO_2$—, or —N($R^7$)$O_2$—, and X: a bond, a lower alkylene, or a lower alkenylene).

7. The pharmaceutical composition according to claim 6, which is an agent for preventing or treating respiratory diseases.

8. The pharmaceutical composition according to claim 7, which is an agent for preventing or treating bronchial asthma.

* * * * *